United States Patent [19]

Sohda et al.

[11] Patent Number: 5,071,841

[45] Date of Patent: Dec. 10, 1991

[54] SULFUR-CONTAINING HETEROCYCLIC COMPOUNDS USEFUL FOR THE TREATMENT OF OSTEOPOROSIS, AND THEIR PRODUCTION

[75] Inventors: Takashi Sohda, Takatsuki; Masao Tsuda, Kobe; Iwao Yamazaki, Takarazuka, all of Japan

[73] Assignee: Takeda Chemical Industries, Ltd., Osaka, Japan

[21] Appl. No.: 458,094

[22] Filed: Dec. 28, 1989

[30] Foreign Application Priority Data

Dec. 28, 1988 [JP] Japan ............................... 63-335240
Nov. 21, 1989 [JP] Japan ............................... 1-303603

[51] Int. Cl.⁵ .................... A61K 31/675; A61K 31/67; C07D 409/00; C07D 495/00

[52] U.S. Cl. ........................................ 514/96; 514/79; 514/212; 514/228.2; 514/233.5; 514/253; 514/275; 514/316; 514/324; 514/361; 514/363; 514/364; 514/365; 514/367; 514/370; 514/377; 514/380; 514/431; 514/432; 540/542; 540/546; 544/57; 544/62; 544/145; 544/240; 544/322; 546/22; 546/187; 546/202; 548/112; 548/128; 548/136; 548/138; 548/156; 548/159; 548/195; 548/233; 548/245; 548/525; 549/5; 549/9; 549/23; 549/51; 549/53

[58] Field of Search ..................... 549/9, 23, 5, 51, 53; 540/596, 542; 514/96, 363, 370, 371, 79, 96, 212, 228.2, 233.5, 275, 316, 324, 361, 363, 364, 365, 367, 370, 377, 380, 431, 432, 253; 544/391, 57, 62, 145, 243, 322; 548/139, 194, 195, 112, 128, 136, 138, 159, 156, 195, 233, 245, 525; 546/22, 187, 202

[56] References Cited

PUBLICATIONS

Neher et al., CA 73-28902b (1970).
Hori et al., CA 111-77940z (1989).
P. H. Bell et al., JACS, vol. 90, p. 2704 (1968).

*Primary Examiner*—Cecilia Shen
*Attorney, Agent, or Firm*—Wegner, Cantor Mueller & Player

[57] ABSTRACT

The present invention provides a sulfur-containing heterocyclic compound of the formula (I)

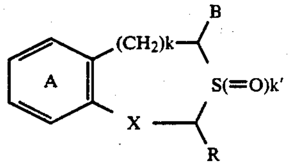

(I)

wherein ring A is a benzene ring which may be substituted; R is a hydrogen atom or a hydrocarbon group which may be substituted; B is a carboxyl group which may be esterified or amidated; X is —CH(OH)— or —CO—; k is 0 or 1; and k' is 0, 1 or 2 or a pharmaceutically acceptable salt thereof.

Also, it provides a process for producing the compound (I) or a salt thereof and a pharmaceutical preparation for use in the treatment of osteoporosis comprising the compound (I) or salt thereof.

The compounds (I) and salts thereof show excellent bone resorption inhibitory activity.

14 Claims, No Drawings

SULFUR-CONTAINING HETEROCYCLIC COMPOUNDS USEFUL FOR THE TREATMENT OF OSTEOPOROSIS, AND THEIR PRODUCTION

BACKGROUND OF THE INVENTION

1. Field of the Invention

The present invention relates to sulfur-containing heterocyclic compounds and salts thereof which are useful for treatment of osteoporosis.

The compounds and salts according to the present invention possess bone resorption inhibitory activity, and they inhibit the quantitative loss of bone due to release of calcium from bones into blood.

2. Description of the Prior Art

Osteoporosis is known as a disease associated with the loss of bone calcium into the blood with the consequent decrease of bone mass which causes the bones to become fragile and liable to be fractured.

The cardinal manifestations of osteoporosis are kyphosis and fracture of thoracic vertebrae, lumber vertebrae, femoral neck, distal ends of radii, ribs, proximal ends of humeri and so on. The cause of such malady varies from endocrine disorder to nutritional disorder. The therapeutic drugs used in such cases are estrogens, calcitonin (calcium regulating hormone), vitamin D, calcium preparations and so on.

However, these therapeutic approaches are not effective enough in that symptoms and patients which can be treated are limited and, moreover, they are not definitely effective in preventing or alleviating the loss of bone mass.

EMBODIMENT OF THE INVENTION

The present invention is therefore directed to: (1) a sulfur-containing heterocyclic compound of the general formula (I)

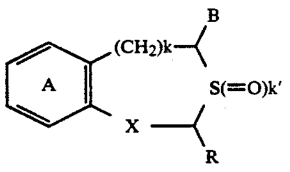

(I)

wherein ring A is a benzene ring which may be substituted; R is a hydrogen atom or a hydrocarbon group which may be substituted; B is a carboxyl group which may be esterified or amidated, X is —CH(OH)— or —CO—; k is 0 or 1; and k' is 0, 1 or 2 or a pharmaceutically acceptable salt thereof.

(2) A process for producing the compound (I) or a salt thereof, which comprises (i) subjecting a compound of the general formula (II)

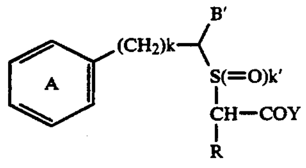

(II)

wherein B' is an esterified carboxyl group; Y is a hydroxy group or a halogen atom and the other symbols respectively have the same meanings as defined above or a salt thereof to cyclization reaction and, if necessary, further to oxidation or/and hydrolysis, hydrolysis followed by amidation, or hydrolysis followed by amidation and oxidation to produce a sulfur-containing heterocyclic compound of the general formula (Ia)

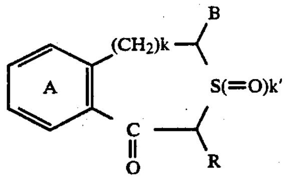

(Ia)

wherein each symbol has the same meaning as defined above or a salt thereof, or alternatively (ii) reducing a compound of the general formula (Ia) defined above or a salt thereof to produce a sulfur-containing heterocyclic compound of the general formula (Ib)

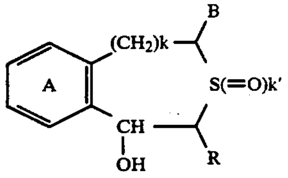

(Ib)

wherein each symbol has the same meaninq as defined above or a salt thereof.

(3) A pharmaceutical preparation for use in the treatment of osteoporosis comprising an effective anti-osteoporotic amount of the compound (I) or pharmaceutically acceptable salt thereof.

In the formula (I), the substituent or substituents on ring A, i.e. the benzene ring which may be substituted, include, among others, halogens, nitro, alkyl groups which may be substituted; hydroxy which may be substituted; thiol which may be substituted, amino, acyl groups, mono- or dialkoxyphosphoryl, phosphono group, aryl groups which may be substituted, aralkyl groups which may be substituted and/or aromatic heterocyclic groups which may be substituted. The benzene ring may be substituted by 1 to 4 and preferably 1 or 2 of such substituents, which may be the same or different.

The halogens mentioned above include fluorine, chlorine, bromine and iodine. The alkyl groups or the alkyl moieties of substituted alkyl groups are preferably straight-chain or branched alkyl groups of 1 to 10 carbon atoms, such as methyl, ethyl, propyl, isopropyl, butyl, isobutyl, sec-butyl, tert-butyl, pentyl, isopentyl, neopentyl, hexyl, heptyl, octyl, nonyl, decyl, etc., and cycloalkyl groups of 3 to 7 carbon atoms, such as cyclopropyl, cyclobutyl, cyclohexyl, cycloheptyl, etc. and these alkyl groups may be substituted by 1 to 3 substituent groups such as halogens (e.g. fluorine, chlorine, bromine and iodine), hydroxy, alkoxy groups of 1 to 6 carbon atoms (e.g. methoxy, ethoxy, propoxy, butoxy and hexyloxy), mono- or di($C_{1-6}$ alkoxy)phosphoryl groups, phosphono group and so on.

Specific examples of such substituted alkyl groups include trifluoromethyl, trifluoroethyl, trichloromethyl, hydroxymethyl, 2-hydroxyethyl, methoxyethyl, 1-methoxyethyl, 2-methoxyethyl, 2,2-diethoxyethyl, 2-diethoxyphosphorylethyl, 2-phosphonoethyl and so on.

The substituted hydroxy includes, among others, alkoxy, alkenyloxy, aralkyloxy, acyloxy and aryloxy. The alkoxy groups mentioned above is preferably a straight-chain or branched alkoxy group of 1 to 10 carbon atoms, such as methoxy, ethoxy, propoxy, butoxy, tert-butoxy, pentyloxy, hexyloxy, heptyloxy, nonyloxy, etc. or a cycloalkoxy group of 4 to 6 carbon atoms, such as cyclobutoxy, cyclopentyloxy, cyclohexyloxy and so on. The alkenyloxy group, also mentioned above, is preferably an alkenyloxy group of 2 to 10 carbon atoms, such as allyloxy, crotyloxy, 2-pentenyloxy, 3-hexenyloxy, 2-cyclopentenylmethoxy, 2-cyclohexenyloxy and so on. The aralkyloxy group is preferably an aralkyloxy group of 6 to 19 carbon atoms and more desirably a $C_{6-14}$ aryl-$C_{1-4}$ alkyloxy group, such as benzyloxy, phenethyloxy and so on. The acyloxy group is preferably an alkanoyloxy group, a $C_{2-10}$ alkanoyloxy group, such as acetyloxy, propionyloxy, n-butyryloxy, hexanoyloxy and so on. The aryloxy group is preferably a $C_{6-14}$ aryloxy group such as phenoxy, biphenyloxy phenyloxy and so on. These groups may be further substituted by 1 to 3 substituent groups such as the above-mentioned halogens, hydroxy, $C_{1-6}$ alkoxy groups and mono- or di-($C_{1-6}$ alkoxy)phosphoryl groups. Specific examples of such substituted hydroxy include trifluoromethoxy, 2,2,2-trifluoroethoxy, difluoromethoxy, 2-methoxyethoxy, 4-chlorobenzyloxy, 2-(3,4-dimethoxyphenyl)ethoxy and so on.

The thiol which may be substituted includes, among others, alkylthio, aralkylthio and acylthio groups. The alkylthio groups are preferably straight-chain or branched $C_{1-10}$ alkylthio groups such as methylthio, ethylthio, propylthio, butylthio, pentylthio, hexylthio, heptylthio, nonylthio, etc. or $C_{4-6}$ cycloalkylthio groups such as cyclobutylthio, cyclopentylthio, cyclohexylthio and so on. The aralkylthio groups are preferably $C_{7-19}$ aralkylthio groups and more desirably $C_{6-14}$ aryl-$C_{1-4}$ alkylthio groups, such as benzylthio, phenethylthio and so on. The acylthio groups are preferably alkanoylthio groups, particularly $C_{2-10}$ alkanoylthio groups, such as acetylthio, propionylthio, n-butyrylthio, hexanoylthio and so on. These groups may be further substituted by 1 to 3 substituent groups such as the above-mentioned halogens, hydroxy, $C_{1-6}$ alkoxy groups and/or mono- or di($C_{1-6}$ alkoxy)phosphoryl groups. Specific examples of said substituted thiol include trifluoromethylthio, 2,2,2-trifluoroethylthio, 2-methoxyethylthio, 4-chlorobenzylthio, 3,4-dichlorobenzylthio, 4-fluorobenzylthio, 2-(3,4-dimethoxyphenyl)ethylthio and so on.

The substituents for said substituted amino include, among others, the above-mentioned $C_{1-10}$ alkyl groups, $C_{2-10}$ alkenyl groups (such as allyl, vinyl, 2-penten-1-yl, 3-penten-1-yl, 2-hexen-1-yl, 3-hexen-1-yl, 2-cyclohexenyl, 2-cyclopentenyl, 2-methyl-2-propen-1-yl, 3-methyl-2-buten-1-yl, etc.), $C_{6-14}$ aryl groups and $C_{7-19}$ aralkyl groups. These substituents may be the same or different and the number of them may be 1 or 2. These substituents may be further substituted by various substituent groups such as the above-mentioned halogens, $C_{1-3}$ alkoxy groups, mono- or di($C_{1-6}$ alkoxy)phosphoryl groups and phosphono group. Specific examples of said substituted amino group include methylamino, dimethylamino, ethylamino, diethylamino, dibutylamino, diallylamino, cyclohexylamino, phenylamino, N-methyl-N-phenylamino, N-methyl-N-(4-chlorobenzyl)amino, N,N-di(2-methoxyethyl)amino and so on.

The acyl group includes acyl groups derived from organic carboxylic acids and those derived from sulfonic acids having $C_{1-6}$ hydrocarbon groups (such as methyl, ethyl, n-propyl, hexyl, phenyl, etc.). The acyl groups derived from organic carboxylic acids include formyl, $C_{1-10}$ alkyl-carbonyl groups (such as acetyl, propionyl, butyryl, valeryl, pivaloyl, hexanoyl, octanoyl, cyclobutanecarbonyl, cyclohexanecarbonyl, cycloheptanecarbonyl, etc.), $C_{2-10}$ alkenyl-carbonyl groups (such as crotonyl, 2-cyclohexenecarbonyl, etc.), $C_{6-14}$ aryl-carbonyl groups (such as benzoyl etc.), $C_{7-19}$ aralkyl-carbonyl groups (such as benzylcarbonyl benzhydrylcarbonyl, etc.), 5- or 6-membered aromatic heterocycle-carbonyl groups (such as nicotinoyl, 4-thiazolylcarbonyl, etc.), 5- or 6-membered aromatic heterocycle-acetyl groups (such as 3-pyridylacetyl, 4-thiazolylacetyl, etc.) and so on. The acyl groups derived from sulfonic acids having $C_{1-6}$ hydrocarbon groups include methanesulfonyl, ethanesulfonyl and so on. These groups may be further substituted by 1 to 3 substituent groups such as the above-mentioned halogens, hydroxy, Cl-6 alkoxy groups, and amino. Specific examples of said substituted acyl groups include trifluoroacetyl, trichloroacetyl, 4-methoxybutyryl, 3-cyclohexyloxypropionyl, 4-chlorobenzoyl, 3,4-dimethoxybenzoyl and so on.

The mono- or di-alkoxyphosphoryl groups mentioned hereinbefore are preferably di-lower alkoxyphosphoryl groups such as dimethoxyphosphoryl, diethoxyphosphoryl, dipropoxyphosphoryl, diisopropoxyphosphoryl, ethylenedioxyphosphoryl, dibutoxyphosphoryl and so on.

The aryl moieties of said substituted aryl groups include, as preferred examples, $C_{6-14}$ aryl groups such as phenyl, naphthyl, anthryl, etc. and these groups may be substituted by 1 to 3 substituent groups such as the above-mentioned $C_{1-6}$ alkyl groups, halogens, hydroxy and $C_{1-6}$ alkoxy groups. Specific examples of such substituted aryl include 4-chlorophenyl, 3,4-dimethoxyphenyl, 4-cyclohexylphenyl, 5,6,7,8-tetrahydro-2-naphthyl and so on.

The aralkyl moiety of said aralkyl group which may be substituted includes, as preferred examples, $C_{7-19}$ aralkyl groups such as benzyl, naphthylethyl, trityl, etc. and these groups may be nuclearly substituted by 1 to 3 substituent groups such as the above-mentioned $C_{1-6}$ alkyl groups, halogens, hydroxy, and $C_{1-6}$ alkosy grups. Specific examples of said substituted aralkyl group include 4-chlorobenzyl, 3,4-dimethoxybenzyl, 4-cyclohexylbenzyl, 2-(5,6,7,8-tetrahydro-2-naphthyl)ethyl and so on.

The aromatic heterocycles of said aromatic heterocyclic groups which may be substituted are preferably 5- or 6-membered aromatic heterocyclic groups containing 1 to 4 nitrogen, oxygen or/and sulfur atoms, such as furyl, thienyl, imidazolyl, thiazolyl, oxazolyl, thiadiazolyl, etc. and these groups may be substituted by 1 to 3 substituent groups such as the above-mentioned $C_{1-6}$ alkyl groups, halogens, hydroxy and $C_{1-6}$ alkoxy groups.

When the benzene ring is substituted by two alkyl groups in adjacent positions, these groups may form an alkylene group of the formula $-(CH_2)_m-$ wherein m is an integer of 3 to 5 (such as trimethylene, tetramethylene and pentamethylene) and when it is substituted by two alkoxy groups in adjacent positions, they may form an alkylenedioxy group of the formula $-O-(CH_2)_n-O-$ where n is an integer of 1 to 3 (such as methylenedioxy, ethylenedioxy and trimethylenedioxy). In such cases, a 5-to 7-membered ring is formed with the carbon atoms of the benzene ring.

The hydrocarbons of said hydrocarbon groups which may be substituted, represented by R, include, among others, the above-mentioned alkyl groups (preferably C1-10 alkyls), alkenyl groups (preferably $C_{2-10}$ alkenyls), aryl groups (preferably $C_{6-14}$ aryls) and aralkyl groups (preferably $C_{7-19}$ aralkyls). The substituents on such hydrocarbons include, among others, the above-mentioned 5-or 6-membered aromatic heterocyclic groups, halogens, dialkoxyphosphoryl groups, phosphono group and so on.

Preferred examples of R are unsubstituted $C_{1-6}$ alkyl groups such as methyl, ethyl, propyl, isopropyl, butyl, isobutyl, sec-butyl, tert-butyl, pentyl, neopentyl, hexyl and so on.

The esterified carboxyl B includes, among others, alkoxycarbonyl groups, preferably $C_{1-10}$ alkoxycarbonyl groups (such as methoxycarbonyl, ethoxycarbonyl, propoxycarbonyl, butoxycarbonyl, etc.), aryloxycarbonyl groups, preferably $C_{6-14}$ aryloxycarbonyl groups (such as phenoxycarbonyl etc.), and aralkyloxycarbonyl groups, preferably $C_{7-19}$ aralkyloxycarbonyl groups (such as benzyloxycarbonyl etc.).

The amidated carboxyl group B is preferably a carbamoyl group of the formula $-CONR_1R_2$ where $R_1$ and $R_2$ each is a hydrogen atom, a hydrocarbon group which may be substituted or a 5- or 7-membered heterocyclic group which may be substituted.

The hydrocarbons of the above-mentioned hydrocarbon groups which may be substituted, $R_1$ and $R_2$, include, among others, alkyl groups, preferably said $C_{1-10}$ alkyl groups, alkenyl groups, preferably said $C_{2-10}$ groups, aryl groups, preferably said $C_{6-14}$ aryl groups, and aralkyl groups, preferably said $C_{7-19}$ aralkyl groups and these groups may be substituted by 1 to 3 substituent groups such as, for example, halogens (such as fluorine, chlorine, bromine and iodine), hydroxy, $C_{1-6}$ alkoxy, amino which may be substituted by $C_{1-6}$ alkyl (such as dimethylamino, diethylamino, dipropylamino, etc.), used as amino substituted by acyl (e.g. $C_{1-10}$ alkanoyl groups) (such as acetylamino, propionylamino, benzoylamino, etc.), carbamoyl which may be substituted by $C_{1-6}$ alkyl (such as dimethylcarbamoyl, ethoxycarbamoyl, dipropylcarbamoyl, etc.), $C_{1-6}$ alkoxycarbonyl (such as methoxycarbonyl, ethoxycarbonyl, propoxycarbonyl, etc.), mono- or dialkoxyphosphoryl (such as dimethoxyphosphoryl etc.), phosphono group and said aromatic heterocyclic groups.

The 5- to 7-membered heterocycles of said 5- to 7-membered heterocyclic groups which may be substitued, $R_1$ and $R_2$, include, among others, 5- to 7-membered heterocycles containing one sulfur, nitrogen or oxygen atom, 5-or 6-membered heterocycles containing 2 to 4 nitrogen atoms, and 5- or 6-membered heterocycles containing 1 to 2 nitrogen atoms and one sulfur or oxygen atom, and each of these heterocycles may be fused to a 6-membered ring containing a maximum of 2 nitrogen atoms, a benzene ring, or a 5-membered ring containing one sulfur atom.

Preferred examples of said 5- to 7-membered heterocyclic groups include pyridyl, pyrimidyl, pyrazinyl, pyridazinyl, pyrazolyl, imidazolyl, thiazolyl, oxazolyl, pyrido[2,3-d]pyrimidyl, benzopyranyl, 1,8-naphthyridinyl, quinolyl, thieno[2,3-b]pyridyl, tetrazolyl, thiadiazolyl, oxadiazolyl, triazinyl, triazolyl, thienyl, pyrrolyl, pyrrolinyl, furyl, pyrrolidinyl, benzothienyl, indolyl, imidazolidinyl, piperidyl, piperidino, piperazinyl, morpholinyl, morpholino and so on.

$R_1$ and $R_2$ may combinedly form a 5- to 7-membered ring, in the manner of

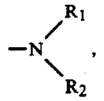

and examples of such ring include morpholine, piperidine, thiomorpholine, homopiperidine, pyrrolidine, thiazolidine, and so on.

Specific examples of said substituted alkyl group, $R_1$ or $R_2$, include trifluoromethyl, trifluoroethyl, difluoromethyl, trichloromethyl, 2-hydroxyethyl, 2-methoxyethyl, 2-ethoxyethyl, 2,2-dimethoxyethyl, 2,2-diethoxyethyl, 2-pyridylmethyl, 3-pyridylmethyl, 4-pyridylmethyl, 2-(2-thienyl)ethyl, 3-(3-furyl)propyl, 2-morpholinoethyl, 3-pyrrolylbutyl, 2-piperidinoethyl, 2-(N,N-dimethyl-amino)ethyl, 2-(N-methyl-N-ethylamino)ethyl, 2-(N,N-di-isopropylamino)ethyl, 5-(N,N-dimethylamino)pentyl, N,N-dimethylcarbamoylethyl, N,N-dimethylcarbamoylpentyl, ethoxycarbonylmethyl, isopropoxycarbonylethyl, tertbutoxycarbonylpropyl, 2-diethoxyphosphorylethyl, 3-dipropoxyphosphorylpropyl, 4-dibutoxyphosphorylbutyl, ethyl-enedioxyphosphorylmethyl, 2-phosphonoethyl, 3-phosphonopropyl, and so on. Specific examples of said substituted aralkyl, representing $R_1$ or $R_2$, are 4-chlorobenzyl, 3-(2-fluorophenyl)propyl, 3-methoxybenzyl, 3,4-dimethoxyphenethyl, 4-ethylbenzyl, 4-(3-trifluorophenyl)butyl, 4-acetylaminobenzyl, 4-dimethylamin 4-diethoxylphosphorylbenzyl, 2-(4-dipropoxylphosphorylmethylphenyl)ethyl and so on. Specific examples of said substituted aryl, representing $R_1$ or $R_2$, include 4-chlorophenyl, 4-cyclohexylphenyl, 5,6,7,8-tetrahydro-2-naphthyl, 3-trifluoromethylphenyl, 4-hydroxyphenyl, 3,4,5-trimethoxyphenyl, 6-methoxy-2-naphthyl, 4-(4-chlorobenzyloxy)phenyl, 3,4-methylenedioxyphenyl, 4-(2,2,2-trifluoroethoxy)phenyl, 4-propionylphenyl, 4-cyclohexanecarbonylphenyl, 4-dimethylaminophenyl, 4-benzoylaminophenyl, 4-diethoxycarbamoylphenyl, 4-tert-butoxycarbonylphenyl, 4-diethoxyphosphorylphenyl, 4-diethoxyphosphorylmethylphenyl, 4-(2-diethoxyphosphorylethyl)phenyl, 2-diethoxyphosphorylmethylphenyl, 3-di-ethoxyphosphorylmethylphenyl, 4-dipropoxyphosphorylphenyl, 4-(2-phosphonoethyl)phenyl, 4-phosphonomethylphenyl, 4-phosphonophenyl and so on. Specific examples of said substituted 5- to 7-membered heterocyclic group, representing $R_1$ or $R_2$, include 5-chloro-2-pyridyl, 3-methoxy-2-pyridyl, 5-methyl-2-benzothiazolyl, 5-methyl4-phenyl-2-thiazolyl, 3-phenyl-5-isooxazolyl, 4-(4-chlorophenyl)-5-methyl-2-oxazolyl, 3-phenyl-1,2,4-thiadiazol-5-yl, 5-methyl-1,3,4-thiadiazol-2-yl, 5-acetylamino-2-pyrimidyl, 3-methyl-2-thienyl, 4,5-dimethyl-2-furanyl, 4-methyl-2-morpholinyl and so on. Among the above-mentioned species, ring A is preferably a benzene ring which may be substituted by halogen, alkyl and/or alkoxy.

The substituent group B is preferably an alkoxycarbonyl group or a group of the formula $-CONR_1R_2$ where $R_1$ and $R_2$ each is a hydrogen atom, a hydrocarbon group which may be substituted or a 5- to 7-membered heterocyclic group which may be substituted.

The substituent R is preferably a hydrogen atom, a $C_{1-8}$ alkyl or a phenyl group.

The compound (I) or a salt thereof can be produced by the per se conventional processes.

For example, the following processes (A through F) may be employed. The salts of the compounds mentioned below are similar to or the same as those of compound (I).

(1) Process A

A compound of general formula (Ia')

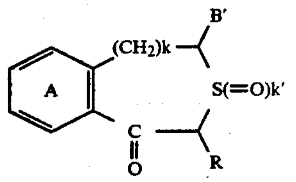

(Ia')

wherein B' is an esterified carboxyl group and the other symbols respectively have the same meanings as defined hereinbefore or a salt thereof can be produced by subjecting a compound of general formula (II) or a salt thereof to cyclization reaction.

The esterified carboxyl group B' may be the same as that defined for B. Thus, B' is preferably an alkyl ester, particularly an ester with a $C_{1-6}$ alkyl group, such as methyl, ethyl, propyl, isopropyl, butyl, tert-butyl, pentyl, neopentyl, hexyl, etc., or an aralkyl ester, particularly an ester with a $C_{7-19}$ aralkyl group, such as benzyl, phenethyl, 3-phenylpropyl and so on.

This cyclization reaction is conducted in the same manner as the usual Friedel-Crafts reaction.

Thus, this cyclization reaction can be carried out by such per se known procedures as those described in Organic Reactions, Vol. 2, page 114, John Wiley & Sons, Inc., N.Y., 1962 and Shin Jikken Kagaku Koza 14, Syntheses and Reactions of Organic Compounds (II), Maruzen, 1977, for instance. To be specific, the reaction can for example be conducted as follows.

This reaction is generally carried out in a solvent which does not interfere with the reaction or in the absence of a solvent.

Examples of the solvent mentioned just above include aromatic hydrocarbons such as benzene, toluene, xylene, etc., halogenated hydrocarbons such as chloroform, dichlormethane, 1,2-dichloroethane, 1,1,2,2-tetrachloroethane, etc., ethers such as diethyl ether, dioxane, tetrahydrofuran, etc., nitrobenzene, nitromethane and carbon disulfide as well as various mixtures thereof.

This reaction is conducted in the presence of a Lewis acid.

Examples of the Lewis acid include hydrogen fluoride, sulfuric acid, phosphoric acid, phosphoric anhydride, aluminum chloride, tin tetrachloride and zinc chloride.

The proportion of such Lewis acid is preferably 2 to 10 moles per mole of compound (II) or a salt thereof. In any case, the reaction temperature is about −20° C. to about 200° C. and preferably about 0° C. to about 100° C. The reaction time is generally about 30 minutes to about 100 hours and preferably about 1 to 30 hours.

(2) Process B

A compound of general formula (Ia")

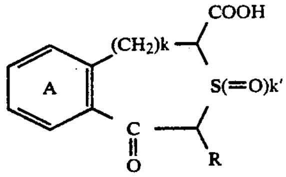

(Ia")

wherein each symbol has the same meaning as defined hereinbefore or a salt thereof can be produced by subjecting compound (Ia') or a salt thereof to a hydrolysis reaction.

This hydrolysis reaction is caried out in an aqueous solvent or water in the conventional manner.

Examples of the aqueous solvent mentioned just above include mixtures of water with alcohols such as methanol, ethanol, etc., ethers such as tetrahydrofuran, dioxane, etc., amides such as N,N-dimethylformamide etc., sulfoxides such as dimethyl sulfoxide etc., or ketones such as acetone, methyl ethyl ketone and so on.

This reaction is conducted in the presence of a base or an acid.

The base mentioned just above may be an inorganic base, exemplified by alkali metal carbonates such as potassium carbonate, sodium carbonate, etc. and alkali metal hydroxides such as sodium hydroxide, potassium hydroxide, lithium hydroxide, etc. or an organic base, exemplified by various alkoxides such as sodium methoxide, sodium ethoxide, potassium tert-butoxide and so on. The acid may be an inorganic acid such as hydrochloric acid, sulfuric acid, hydrobromic acid, etc. or an organic acid such as acetic acid, trifluoroacetic acid and so on. The acid or base is preferably used in excess with respect to compound (Ia'). The preferred proportion of the base is about 1.2 to 6 equivalents based on compound (Ia'). The preferred proportion of the acid is about 2 to 50 equivalents based on compound (Ia').

This reaction is conducted generally at about −20° C. to about 150° C. and preferably at about −10° C. to about 100° C.

(3) Process C

A compound of general formula (Ic)

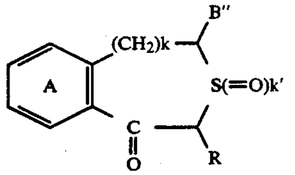

(Ic)

wherein B" is an amidated carboxyl group and the other symbols respectively have the same meanings as defined hereinbefore or a salt thereof can be produced by subjecting compound (Ia") or a salt thereof to amidation reaction.

This reaction is carried out by reacting compound (Ia") or a salt thereof with an amine compound.

The amine compound is preferably a compound of the following general formula (III)

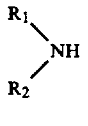

(III)

wherein each symbol has the same meaning as defined hereinbefore. This reaction between compound (Ia'') or salt thereof and amine compound is conducted in the same manner as the condensation reaction well known in the field of peptide synthesis.

This reaction can thus be carried out by the various per se known processes described in M. Bodansky and M. A. Ondetti: Peptide Synthesis, Interscience, New York, 1966, F. M. Finn and K. Hofmann: The Proteins, Vol. 2, edited by H. Nenrath & R.L. Hill, Academic Press New York, 1976, and Nobuo Izumiya et al.: Peptide Gosei no Kiso to Zikken, Maruzen, 1985, for instance, namely the acyl azide method, acyl chloride method, acid anhydride method, mixed anhydride method, DCC method, activated ester method, Woodward,s reagent K method, carbonyldiimidazole method, redox process, DCC/HONB method and so on.

Thus, for example, this reaction can be carried out under the following conditions.

The starting material amine compound may be used in a proportion of about 1 to 10 moles per mole of compound (Ia'') or a salt thereof.

This reaction is conducted in a solvent which does not interfere with the reaction.

Examples of such solvent include amides such as dimethylformamide etc., sulfoxides such as dimethyl sulfoxide etc., pyridines such as pyridine, picoline, lutidine, etc., halogenated hydrocarbons such as chloroform, dichloromethane, etc., ethers such as tetrahydrofuran etc. and nitriles such as acetonitrile etc., as well as appropriate mixtures of such solvents. These solvents can be used in anhydrous or hydrous condition.

The reaction temperature is generally about −20° C. to about 50° C. and preferably about −10° C. to about 30° C. The reaction time is about 1 to 100 hours and preferably about 2 to 40 hours.

(4) Process D

A compound of general formula (Id)

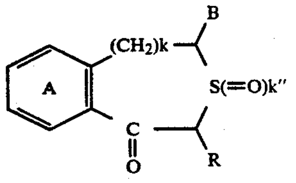

(Id)

wherein k is 1 or 2 and the other symbols respectively have the same meanings as defined hereinbefore or a salt thereof can be produced by subjecting a compound (Ia'), (Ia'') or (Ic), wherein k, is invariably equal to 0, or a salt thereof to an oxidation reaction.

This oxidation reaction is carried out by the usual oxidation procedure using an oxidizing agent.

The oxidizing agent to be used for this reaction is a mild oxidizing agent which does not substantially affect the skeletal structure of sulfur-containing heterocyclic compounds, such as perbenzoic acid, m-chloroperbenzoic acid, hydrogen peroxide, peresters, sodium metaperiodate, phenyl dichloroiodide, ozone, hydrogen peroxide and sodium hypochlorite, to mention only a few preferred examples.

This reaction is conducted in an organic solvent that will not interfere with the reaction.

The solvent mentioned just above includes, among others, aromatic hydrocarbons such as benzene, toluene, xylene, etc., halogenated hydrocarbons such as chloroform, dichloromethane, 1,2-dichloroethane, 1,1,2,2-tetrachloroethane, etc., ethers such as diethyl ether, dioxane, tetrahydrofuran, etc., and alcohols such as methanol, ethanol, propanol, etc., inclusive of various mixtures of such solvents.

The use of the above oxidizing agent in an equimolar or subequimolar proportion to compound (Ia'), (Ia'') or (Ic), wherein k' is 0, or a salt thereof, results preferentially in the formation of compound (Id) wherein k'' is 1. The compound (Id) wherein k'' is 2 is formed when the oxidizing agent is available in excess, in which case the compound (Id) wherein k'' is 1 is further oxidized.

This reaction proceeds at or below room temperature (30°–20° C.). The preferred reaction temperature is about −50° C. to about 20° C.

The reaction time is about 30 minutes to about 10 hours.

(5) Process E

A compound of general formula (Ib) or a salt thereof can be produced by subjecting compound (Ia'), (Ia''), (Ic) or (Id), or a salt thereof, to a reduction reaction.

This reaction is a reaction starting with a compound prepared by any of Processes A through D to produce a compound of general formula (I) wherein X is —CH(OH)—, that is to say compound (Ib) or a salt thereof.

This reaction can be conducted by a per se known reduction process, for example by the procedures described in Shin Jikken Kagaku Koza, 15 - Oxidation and Reduction [II], Maruzen, 1977.

For example, this reaction is carried out by treating compound (Ia'), (Ia''), (Ic) or (Id), or a salt thereof, with a reducing agent.

As the reducing agent, use may be made of metals and metal salts, for example metal hydrogen complex compounds such as alkali metal borohydrides, e.g. sodium borohydride, lithium borohydride, etc., metal hydrides such as sodium hydride etc., organic tin (e.g. triphenyltin hydride etc.), nickel and zinc compounds, and catalytic reduction systems comprising transition metal catalysts such as palladium, platinum, rhodium, etc. in combination with hydrogen.

This reaction is conducted in an organic solvent which will not interfere with the reaction.

The solvent mentioned just above includes, among others, aromatic hydrocarbons such as benzene, toluene, xylene, etc., halogenated hydrocarbons such as chloroform, dichloromethane, 1,2-dichloroethane, 1,1,2,2-tetrachloroethane, etc., ethers such as diethyl ether, dioxane, tetrahydrofuran, dimethylene glycol monomethyl ether, etc., alcohols such as methanol, ethanol, propanol, etc., and amides such as dimethylformamide etc., and these solvents are selectively used according to the type of reducing agent.

The reaction temperature is 0° C. to 130° C. and preferably 10° C. to 100° C.

The reaction time approximately ranges from 1 to 24 hours.

(6) Process F

This is a process for producing a phosphono group-containing compound or a salt thereof from a monoalkoxy- or a dialkoxyphosphoryl group-containing compound which is among the compounds synthesized in processes A through E.

This reaction is carried out with an inorganic acid, such as hydrochloric acid, hydrobromic acid, etc., or a trialkylsilyl halide in a solvent which does not interfere with the reaction.

When an inorganic acid, such as hydrochloric acid, hydrobromic acid, etc., is employed, the solvent may be an alcohol, such as methanol, ethanol, 2-methoxyethanol, ethylene glycol, propanol, butanol, etc., or water or a mixture thereof. The acid is generally used in large excess and the reaction time is generally 10° to 150° C. and preferably about 30° to 100° C. The reaction time is 1 to 50 hours.

When an alkylsilyl halide, such as chlorotrimethylsilane, bromotrimethylsilane, iodotrimethylsilane, etc., is employed, the solvent may be a halogenated hydrocarbon, such as carbon tetrachloride, chloroform, dichloromethane, 1,2-dichloroethane, 1,1,2,2-tetrachloroethane, etc., or acetonitrile or a mixture thereof.

The proportion of the alkylsilyl halide is generally 1 to 10 equivalents and preferably 2 to 5 equivalents based on the monoalkoxy- or dialkoxyphosphoryl group-containing compound. The reaction temperature is generally −30° C. to 100° C. and preferably −10° C. to 50° C., and the reaction time is 30 to 100 hours.

The resulting sulfur-containing heterocyclic compound can be isolated and purified by the well-known separation and purification procedures such as concentration, concentration under reduced pressure, solvent extraction, crystallization, recrystallization, redistribution, chromatography and so on. The same separation and purification procedures are also applicable to the preparation of the starting compound described below.

The starting compound (II) for the present invention can be prepared by a known method or a method analogous thereto, for example by the following process.

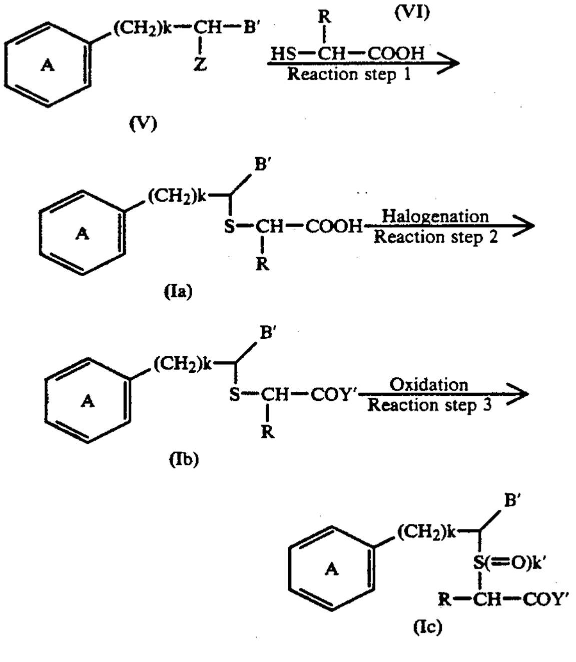

(VI) (V) (Ia) (Ib) (Ic)

In the above formulas, Z is a leaving group; Y' is a halogen atom; and the other symbols respectively have the same meanings as defined hereinbefore.

REACTION STEP 1

In this reaction step, compound (V) or a salt thereof is reacted with compound (VI) or a salt thereof in the presence of a base to give compound (IIa) or a salt thereof.

Examples of said leaving group Z include halogens, preferably chlorine, bromine and iodine, and hydroxyl groups activated by esterification, such as organic sulfonic acid residues (e.g. p-toluenesulfonyloxy), $C_{1-4}$ alkylsulfonyloxy (e.g. methanesulfonyloxy) and organic phosphoric acid residues such as diphenylphosphoryloxy, dibenzylphosphoryloxy, dimethylphosphoryloxy and so on.

The reaction of compound (V) or a salt thereof with compound (VI) or a salt thereof is conducted in a solvent which does not interfere with the reaction.

Examples of such solvent include aromatic hydrocarbons such as benzene, toluene, xylene, etc., ethers such as dioxane, tetrahydrofuran, dimethoxyethane, etc., alcohols such as methanol, ethanol, propanol, etc., esters such as ethyl acetate etc., nitriles such as acetonitrile etc., pyridines such as pyridine, lutidine, etc., amides such as N,N-dimethylformamide etc., sulfoxides such as dimethyl sulfoxide etc., halogenated hydrocarbns such as chloroform, dichloromethane, 1,2-dichloroethane, 1,1,2,2-tetrachloroethane, etc., and ketones such as acetone, 2-butanone, etc., as well as various mixtures of such solvents.

This reaction is conducted in the presence of an inorganic base, such as sodium hydroxide, potassium hydroxide, potassium carbonate, sodium carbonate, sodium hydrogen carbonate, etc. or an organic base such as amines, e.g. pyridine, triethylamine, N,N-dimethylaniline and so on.

The preferred proportion of such base is about 1 to 5 moles per mole of compound (V) or a salt thereof.

This reaction is conducted generally at −20° C. to about 150° C. and preferably at about −10° C. to about 100° C.

The starting compound (V) or salt thereof can be synthesized, for example by the processes described in Chem. Pharm. Bull. 30, 3580 (1982) and Chem. Pharm. Bull. 30, 3601 (1982).

REACTION STEP 2

In this step, compound (IIa) or a salt thereof is halogenated to give compound (IIb) or a salt thereof.

This reaction can be conducted by the per se known processes.

For example, the reaction can be carried out by the processes described in Shin Zikken Kagaku Koza 14, Syntheses and Reactions of Organic Compounds [II], Maruzen, 1977.

Thus, for example, this reaction can be conducted by reacting compound (IIa) or a salt thereof with a halogenating agent such as a chlorinating agent (e.g. phosphorus pentachloride, thionyl chloride, oxalyl chloride, etc.).

The reaction is conducted in a solvent which does not interfere with the reaction or in the absence of a solvent.

The solvent mentioned just above includes, among others, aromatic hydrocarbons such as benzene, toluene, xylene, etc., ethers such as dioxane, tetrahydrofuran, dimethoxyethane, etc., nitriles such as acetonitrile, amides such as N,N-dimethylformamide etc. and halogenated hydrocarbons such as chloroform, dichloromethane, 1,2-dichloroethane, 1,1,2,2-tetrachloroethane, etc., as well as various mixtures of such solvents. This reaction is carried out under heating (35° C. to 120° C.). The reaction time approximately ranges from 1 to 20 hours.

REACTION STEP 3

In this step, compound (IIb) or a salt thereof is subjected to an oxidation reaction to give compound (IIc) or a salt thereof.

This reaction is conducted in the same manner as process D.

The compound (IIa) can also be synthesized by the following process.

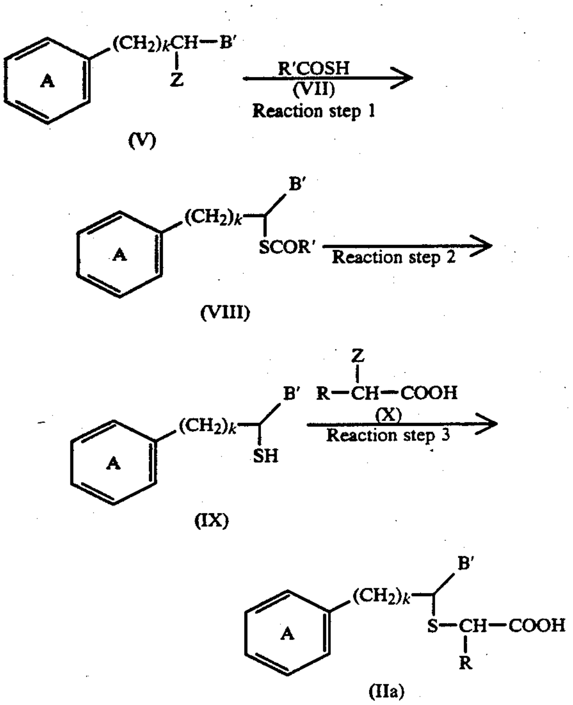

In the above formulas, R' means a lower alkyl group and all other symbols are respectively as defined hereinbefore.

REACTION STEP 1

This is a reaction step where compound (V) is reacted with compound (VII) or a salt thereof in the presence of a base to give compound (VIII).

Examples of leaving group Z include the groups mentioned hereinbefore. Examples of lower alkyl group R' are $C_{1-4}$ alkyl groups such as methyl, ethyl, propyl, isopropyl, butyl, isobutyl and so on.

The reaction of compound (V) with compound (VII) or a salt thereof is conducted in a solvent which does not interfere with the reaction.

Examples of such solvent include aromatic hydrocarbons, such as benzene, toluene, xylene, etc., ethers such as dioxane, tetrahydrofuran, dimethoxyethane, etc., esters such as ethyl acetate etc., amides such as N,N-dimethylformamide etc., sulfoxides such as dimethyl sulfoxide etc., halogenated hydrocarbons such as chloroform, dichloromethane, 1,2-dichloroethane, 1,1,2,2-tetrachloroethane, etc., and ketones such as acetone, 2-butanone, etc., and appropriate mixtures thereof.

This reaction is conducted in the presence of an inorganic base, such as sodium hydroxide, potassium hydroxide, potassium carbonate, sodium hydrogen carbonate, etc., or an organic base, such as pyridine, triethylamine, N,N-dimethylaniline and so on.

The proportion of such base is preferably about 1 to 5 moles per mole of compound (V).

This reaction is conducted generally at −20° C. to 150° C. and preferably at about −10° C. to 100° C. The reaction time is generally 30 minutes to 10 hours.

REACTION STEP 2

This is a reaction step where compound (VIII) is hydrolyzed in the presence of a base to give compound (IX).

This reaction is conducted in a solvent which does not interfere with the reaction. Examples of such solvent are alcohols, such as methanol, ethanol, propanol, isopropyl alcohol, 2-methoxyethanol, etc., and mixtures of water with such alcohols, tetrahydrofuran, acetone, N,N-dimethylformamide, dimethyl sulfoxide and so on.

This reaction is conducted in the presence of an inorganic base such as sodium hydroxide, potassium hydroxide, potassium carbonate, etc., ammonia, or an organic base such as secondary amines, e.g. dimethylamine, diethylamine, morpholine, piperidine, etc., and so on.

The preferred proportion of such base is about 1 to 10 moles per mole of compound (VIII).

This reaction is conducted generally at −20° C. to 0° C. and preferably about −10° C. to 80° C.

REACTION STEP 3

This is a reaction step where compound (IX) or a salt thereof is reacted with compound (X) or a salt thereof in the presence of a base to give compound (IIa) or a salt thereof.

Examples of leaving group Z are hydroxyl groups activated by halogen, preferably chlorine, bromine or iodine, or by esterification, such as organic sulfonic acid residues (e.g. p-toluenesulfonyloxy), $C_{1-4}$ alkylsulfonyloxy (e.g. methanesulfonyloxy), and organic phosphoric acid residues such as diphenylphosphoryloxy, dibenzylphosphoryloxy, dimethylphosphoryloxy and so on.

The reaction of compound (IX) or a salt thereof with compound (X) or a salt thereof is conducted in a solvent which does not interfere with the reaction.

Examples of such solvent are aromatic hydrocarbons such as benzene, toluene, xylene, etc., ethers such as dioxane, tetrahydrofuran, dimethoxyethane, etc., alcohols such as methanol, ethanol, propanol, etc., esters such as ethyl acetate etc., nitriles such as acetonitrile etc., pyridines such as pyridine, lutidine, etc., amides such as N,N-dimethylformamide etc., sulfoxides such as dimethyl sulfoxide etc., halogenated hydrocarbons such as chloroform, dichloromethane, 1,2-dichloroethane, 1,1,2,2-tetrachloroethane, etc., ketones, such as acetone, 2-butanone, etc. and appropriate mixtures thereof.

This reaction is conducted in the presence of an inorganic base, such as sodium hydroxide, potassium hydroxide, potassium carbonate, sodium carbonate, sodium hydrogen carbonate, etc., or an organic base such as a tertiary amine, e.g. pyridine, triethylamine, N,N-dimethylaniline and so on.

The proportion of such base is preferably about 1 to 5 moles per mole of compound (IX).

This reaction is conducted generally at −20° C. to 150° C. and preferably at about −10° C. to 100° C.

As the salt of compound (I) according to the invention, a pharmaceutically acceptable salt is preferably used. The pharmaceutically acceptable salt includes, among others, salts with inorganic bases, salts with organic bases, salts with organic acids and salts with basic or acid amino acids. The inorganic bases include, among others, alkali metals (e.g. sodium, potassium, etc.) and alkaline earth metals (e.g. calcium, magnesium, etc.) and the organic bases include, among others, trimethylamine, triethylamine, pyridine, picoline, N,N-dibenzylethylenediamine, diethanolamine and so on. The inorganic acids mentioned above include, among others, hydrochloric acid, hydrobromic acid, hydroiodic acid, phosphoric acid, nitric acid, sulfuric acid, etc. and the organic acids also mentioned above include, among others, formic acid, acetic acid, trifluoroacetic acid, oxalic acid, tartaric acid, fumaric acid, maleic acid, methanesulfonic acid, benzenesulfonic acid, p-toluenesulfonic acid, citric acid and so on. The basic or acidic amino acids include arginine, lysine, aspartic acid, glutamic acid, etc., to name but a few.

Among the various types of salts mentioned above, said salts with bases mean salts which are formed when compound (I) contains a carboxyl group for B and/or an acidic group such as carboxyl or sulfo on ring A or in the substituent gruop B or R, and said salts with acids mean any and all salts formed when compound (I) contains a basic group such as amino on ring A or in the substituent B or R.

The toxicity of compound (I) and its salt are very low For example, when the compounds synthesized in Example Nos. 18 and 22 were administered orally in a dose of 300 mg/kg to mice, no death was encountered. The compound (I) and salt according to the present invention has excellent bone resorption inhibitory activity. Thus, they have the action to inhibit the dissolution and diminution of bone in the body. Furthermore, compound (I) and salts thereof have bone formation promoting activity.

Therefore, compound (I) and salts according to the present invention can be used, as a drug for man and domestic animals, safely in the prevention and treatment of various diseases arising from bone resorption, such as osteoporosis.

Compound (I) and salts thereof can be administered orally or otherwise (for example by intravenous or intramuscular injection).

Usual dosage forms for oral administration include solid and liquid forms, such as tablets (inclusive of sugar-coated and film-coated tablets), pills, granules, powders, capsules (including soft capsules), syrups, elixirs, emulsions, suspensions and so on.

These oral dosage forms can be manufactured by the per se known procedures diluting the compound (I) or a pharmaceutically acceptable salt thereof with the carriers or excipients used commonly in parmaceutical practice.

Examples of said carriers or excipients include binders such as syrup, gum arabic, gelatin, sorbitol, gum tragacanth, polyvinylpyrrolidone, etc., fillers such as lactose, sucrose and other sugars, corn starch, calcium phosphate, glycine, etc., lubricating agents such as magnesium stearate, talc, polyethylene glycol, silica, etc., disintegrating agents such as potato starch, and wetting agents such as sodium laurylsulfate and so on.

The dosage forms for parenteral administration include, among others, various injectable preparations (e.g. subcutaneous, intradermal, intramuscular and other injections), suppositories and so on.

The injectable preparations can be manufactured by the per se known procedures, for example by suspending or emulsifying compound (I) or a salt thereof in a sterile aqueous or oily vehicle. The aqueous vehicle for injections include, among others, physiological saline and various isotonic solutions and, if necessary, suitable suspending agents such as carboxymethylcellulose sodium or nonionic surfactants can be employed in the preparation of injections. The oily vehicle may for example be sesame oil or soybean oil, and as a cosolvent, benzyl benzoate, benzyl alcohol or the like can be used. The injections so prepared are generally filled into suitable ampules.

It is also possible to incorporate in such a preparation a different active ingredient showing bone resorption inhibitory activity (for example, Ipriflavone ®) to provide a product showing a still more potent bone resorption inhibitory effect.

Compound (I) or a salt thereof can be used as a prophylactic and therapeutic agent for diseases arising from bone resorption, such as osteoporosis. While the daily dosage of compound (I) or a salt thereof depends on the patient,s condition and body weight, method of administration, and other factors, the oral dosage for an adult human (weighing about 50 kg) is 1 to 500 mg, preferably 15 to 300 mg, as active ingredient (compound (I) or a salt thereof) and this dosage is administered in a single dose to 3 divided doses a day.

EFFECTS OF THE INVENTION

Compound (I) or a salt thereof, which is provided by the present invention, has potent bone resorption inhibitory, bone metabolism improving, and bone formation promoting activities and is used in the prevention and treatment of various diseases arising from bone resorption, such as osteoporosis, in man and animals.

Compound (I) or a salt thereof of the present invention, is only sparingly toxic and can be safely used.

The following test, reference examples and working examples are intended to illustrate the present invention in further detail and are by no means limitative of the scope of the invention.

TEST 1

Study on Bone Resorption Inhibition

Bone resorption inhibitory activity was determined accordng to the method of Raisz [Journal of Clinical Investigation (J. Clin. Invest.) 44, 103–116 (1965)].

Thus, a Sprague-Dawley rat at day 19 of pregnancy was subcutaneously dosed with 50 $\mu$Ci of $^{45}$Ca (a radioisotope of calcium, in $CaCl_2$). On the next day, the animal was laparotomized and the fetuses were removed aseptically. The right and left humeri (radii and ulnae) of each rat fetus were dissected from the body under the dissection microscope. The connective tissue and cartilages were removed as far as possible to prepare bone culture specimens. Each piece of bone was incubated in 0.6 ml of $BGJ_b$ medium Fitton-Jackson modification (the tradename owned by GIBCO Laboratories, U.S.A.) containing 2 mg/ml of bovine serum albumin at 37° C. for 24 hours. Then, incubation was carried out for two additional days in the above-mentioned medium to which the test compound had been added at a final concentration of 10 $\mu$g/ml. The radioactivities of $^{45}$Ca in the culture medium and bone were determined and the ratio (%) of $^{45}$Ca released from the bone to the medium was calculated according to the following formula.

$$A = \frac{B}{B + C} \times 100$$

A = ratio (%) of $^{45}$Ca released from the bone to the medium

B = $^{45}$Ca count in the medium

C=$^{45}Ca$ count in the bone

The bones from the fetuses of the same litter were similarly incubated without addition of the test compound for two days and served as controls.

The values for 5 bones per group were expressed in mean. The ratio (%) of this value for the treatment group to the control value was determined. The results are shown in Table 1.

TABLE 1

| Example No. | $^{45}Ca$ released (% of control value) |
|---|---|
| 1 | 84 |
| 10 | 62 |
| 12 | 84 |
| 14 | 81 |
| 19 | 70 |
| 21 | 73 |
| 22 | 57 |
| 23 | 65 |
| 28 | 79 |
| 30 | 75 |
| 31 | 64 |
| 33 | 53 |
| 35 | 58 |
| 36 | 73 |
| 46 | 76 |
| 50 | 73 |
| 55 | 78 |
| 56 | 76 |
| 59 | 64 |
| 63[1] | 79 |
| 63[2] | 86 |
| 127 | 69 |
| 128 | 76 |
| 131 | 69 |
| 132 | 57 |
| 133 | 79 |
| 136 | 67 |
| 138 | 63 |
| 140 | 61 |
| 141 | 57 |
| 143 | 44 |
| 144 | 52 |
| 146 | 62 |
| 150 | 71 |
| 153 | 63 |
| 155 | 80 |
| 157 | 71 |
| 160 | 54 |
| 161 | 50 |
| 163 | 50 |
| 167 | 48 |
| 174 | 73 |
| 176 | 82 |
| 183 | 47 |
| 191 | 58 |
| 198 | 62 |
| 201 | 65 |

Note [1]2-oxide
Note [2]2,2-dioxide

Table 1 shows that the compound according to the present invention inhibited the release of $^{45}Ca$ by 44–86% as compared with the control, thus producing an excellent bone resorption inhibitory effect.

TEST 2

Study on Treatment of Osteoporosis

Oophorectomy was performed on Sprague-Dawley rats at 10 weeks of age and starting from the following day, the rats were orally dosed with the test compound 6 days a week for 3 weeks, or a total of 18 days. On the day following the last dosing, the right femur was removed from each rat and subjected to soft X-ray photography with a soft X-ray apparatus (Softex CSM, Softex). Using a microdensitometer (PDM-5, Konica Medical), the transverse section of the femur on the soft X-ray film was scanned at a point one-fifth from the distal end (metaphysis) and from the density wave pattern, bone density was calculated according to the microdensitometric method described by Inoue et al. [Journal of Japanese Orthopedic Association (J Jpn. Orthop. Ass.) 57, 1923 (1983)].

After soft X-ray photographing, the ⅓ distal part of the femur was sectioned off at right angles with the major axis. After the bone marrows were washed off with a rinse pump, the femur section was put into a porcelain crucible, placed in a oven and dried at 110° C. for 24 hours. The dry weight was then determined.

The porcelain crucible containing the bone was transferred to a muffle furnace (FP-41, Yamato Chemicl) and heated at 500° C. for 3 hours and at 800° C. for 2 hours for calcification of the bone and the ashes were weighed.

The mean ± standard errors of the measured values for the right femurs of 7 rats per group were determined. The results are shown in Table 2 through 4.

TABLE 2

| Group | Daily dose (mg/kg) | Bone density | Dry weight (mg) | Ashes (mg) |
|---|---|---|---|---|
| Sham operation Control | 0 | 1.304 ± 0.021** | 116.2 ± 2.6 | 80.0 ± 2.0 |
| Oophorectomy Control | 0 | 1.062 ± 0.035 | 107.7 ± 3.3 | 74.3 ± 2.2 |
| Compound (Example No. 22) Treatment group | 100 | 1.336 ± 0.072** | 120.0 ± 3.4* | 82.4 ± 2.4* |

*$p < 0.05$
**$p < 0.01$ (compared with oophorectomized controls)

TABLE 3

| Group | Daily dose (mg/kg) | Dry weight (mg) | Ashes (mg) |
|---|---|---|---|
| Sham operation Control | 0 | 130.4 ± 4.4* | 88.3 ± 2.5** |
| Oophorectomy Control | 0 | 112.3 ± 3.7 | 74.3 ± 2.5 |
| Compound (Example No. 146) Treatment group | 100 | 128.2* ± 5.0 | 84.1 ± 3.5 |

*$p < 0.05$
**$p < 0.01$

TABLE 4

| Group | Daily dose (mg/kg) | Dry weight (mg) | Ashes (mg) |
|---|---|---|---|
| Sham operation Control | 0 | 131.4 ± 2.1** | 85.7 ± 1.3** |
| Oophorectomy Control | 0 | 114.2 ± 3.6 | 76.3 ± 2.2 |
| Compound (Example No. 163) Treatment group | 100 | 127.6* ± 3.7 | 82.3 ± 2.1 |
| Compound (Example No. 161) Treatment group | 100 | 127.5* ± 4.3 | 83.7 ± 3.0 |

*$p < 0.05$
**$p < 0.01$

It is apparent from Table 2 through 4 that the compound of the present invention is effective in preventing the decrease of bone mass and suppressing the in vivo release of calcium from the bones.

The symbols used below in the reference and working examples have the following meanings. s:singlet, d:doublet, t:triplet, q:quartet, d,d:double doublet, m:multiplet, br:broad, J:coupling constant, THF:tetrahydrofuran, DMF:N,N-dimethylformamide

REFERENCE EXAMPLE 1

To an ice-cooled suspension of aluminum chloride (48.0 g) in dichloromethane (500 ml) were added dropwise ethyloxalyl chloride (48.0 g) and phenylcyclohexane (48.0 g) in that order, and the mixture was stirred with icecooling for 30 minutes. The reaction mixture was then poured into ice-water and the organic layer was separated. The aqueous layer was extracted with chloroform and the extract was combined with the organic layer. The organic solution was then washed with water, dried ($MgSO_4$) and subjected to distillation in vacuo to give ethyl 4-cyclohexylphenylglyoxylate (68.0 g, yield 87%). bp 163°-165° C./0.3 mmHg NMR (δ ppm, $CDCl_3$): 1.40(3H, t, J=7 Hz), 1.4-2.1 (8H, m), 2.60 (1H, m), 4.43 (2H, q, J=7 Hz), 7.34 (2H, d, J=9 Hz), 7.96 (2H, d, J=7 Hz).

REFERENCE EXAMPLE 2

In the same manner as Reference Example 1, ethyl 5,6,7,8-tetrahydro-2-naphthylglyoxylate was obtained. Yield 80%.

bp. 152°-154° C./0.5 mmHg NMR (δ ppm, $CDCl_3$): 1.41 (3H, t, J=7 Hz), 1.8 (4H, m), 2.8 (4H, m), 4.44 (2H, q, J=7 Hz), 7.18 (1H, q, J=9 Hz), 7.7 (2H, m).

REFERENCE EXAMPLE 3

In the same manner as Reference Example 1, ethyl 3,4-dimethoxyphenylglyoxylate was obtained. Yield 78%.

bp. 158°-160° C./0.1 mmHg

NMR (δ ppm, $CDCl_3$): 1.38 (3H, t, J=7 Hz), 3.93 (3H, s), 3.95 (3H, s), 4.41 (2H, q, J=7 Hz), 6.91 (1H, d, J=8 Hz), 7.5-7.7 (2H, m).

REFERENCE EXAMPLE 4

In the same manner as Reference Example 1, ethyl 3,4-ethylenedioxyphenylglyoxylate was obtained. Yield 86%.

bp. 172°-175° C./0.5 mmHg

REFERENCE EXAMPLE 5

In the same manner as Reference Example 1, ethyl 4-hexylphenylglyoxylate was obtained. Yield 84%.

bp. 160°-162° C./0.5 mmHg

NMR (δ ppm, $CDCl_3$): 0.87 (3H, t, J=7 Hz), 1.40 (3H, t, J=7 Hz), 1.2-1.8 (8H, m), 2.67 (2H, t, J=7 Hz), 4.33 (2H, q, J=7 Hz), 7.28 (2H, d, J=9 Hz), 7.90 (2H, d, J=9 Hz).

REFERENCE EXAMPLE 6

A solution of sodium borohydride (2.0 g) in ethanol (100 ml) was added dropwise to an ice-cooled solution of ethyl 5,6,7,8-tetrahydro-2-naphthylglyoxylate (34.5 g) in ethanol (200 ml). After completion of dropwise addition, acetic acid (6 ml) was added and the reaction mixture was poured into water and extracted with chloroform. The chloroform layer was washed with water, dried ($MgSO_4$) and the solvent was distilled off to give ethyl 2-hydroxy-(5,6,7,8-tetrahydro-2-naphthyl)acetate (34.5 g, yield 9%) as an oil.

NMR δ ppm, $CDCl_3$): 1.22 (3H, t, J=7 Hz), 1.8 (4H, m), 2.7 (4H, m), 3.32 (1H, d, J=6 Hz), 4.0-4.4 (2H, m), 7.1 (3H, m).

REFERENCE EXAMPLE 7

In the same manner as Reference Example 6, ethyl 2-hydroxy-2-(4-cyclohexylphenyl)acetate was obtained. Yield 83%.

mp. 85°-86° C. (ethanol)

Elemental analysis: $C_{16}H_{22}O_3$

Calcd.: C, 73.25; H, 8.45.

Found : C, 73.26; H, 8.46.

REFERENCE EXAMPLE 8

In the same manner as Reference Example 6, ethyl 2-hydroxy-2-(3,4-dimethoxyphenyl)acetate was obtained as an oil. Yield 82%. NMR (δ ppm, $CDCl_3$): 1.21 (3H, t, J=7 Hz), 3.10 (1H, d, J=6Hz), 3.87 (6H, s), 4.21 (2H, q, J=7 Hz), 5.07 (1H, d, J=6 Hz), 6.7-7.0 (3H, m).

REFERENCE EXAMPLE 9

In the same manner as Reference Example 6, ethyl 2-hydroxy-2-(3,4-ethylenedioxyphenyl)acetate was obtained as an oil. Yield 74%.

NMR (δ ppm, $CDCl_3$): 1.24 (3H, t, J=7 Hz), 3.41 (1H, d, J=6 Hz), 4.1-4.4 (2H, m), 4.26 (4H, s), 5.04 (1H, d, J=6 Hz), 6.8-7.0 (3H, m).

REFERENCE EXAMPLE 10

In the same manner as Reference Example 6, ethyl 2-hydroxy-2-(4-hexylphenyl)acetate was obtained as an oil. Yield 98%.

NMR (δ ppm, $CDCl_3$): 0.86 (3H, t, J=7 Hz), 1.24 (3H, t, J=7 Hz), 1.1-1.8 (8H, m), 2.60 (2H, t, J=7 Hz), 4.0-4.4 (2H, m), 5.11 (1H, s), 7.13 (2H, d, J=9 Hz), 7.32 (2H, d, J=9 Hz).

REFERENCE EXAMPLE 11

To ethyl 2-hydroxy-2-(4-cyclohexylphenyl)acetate (52 g) was added thionyl chloride (100 ml) and the mixture was refluxed for 1 hour. The reaction mixture was then concentrated under reduced pressure, and the residual oil was diluted with water and extracted with ether. The ether layer was washed with water, dried ($MgSO_4$) and subjected to vacuum distillation to give ethyl 2-chloro-2-(4-cyclohexylphenyl)acetate (50 g, yield 89%).

bp. 160°-162° C./0.5 mmHg

NMR (δ ppm, $CDCl_3$): 1.24 (3H, t, J=7 Hz), 1.2-2.0 (10H, m), 2.5 (1H, m), 4.21 (2H, q, J=7 Hz), 5.3 (1H, s), 7.18 (2H, d, J=9 Hz), 7.40 (2H, d, J=9 Hz).

REFERENCE EXAMPLE 12

In the same manner as Reference Example 11, ethyl 2-chloro-2-(5,6,7,8-tetrahydro-2-naphthyl)acetate was obtained as an oil. Yield 89%.

bp. 139°-141° C./0.5 mmHg

NMR (δ ppm, $CDCl_3$): 1.24 (3H, t, J=7 Hz), 1.8 (4H, m), 2.7 (4H, m), 4.21 (2H, q, J=7 Hz), 5.26 (1H, s), 7.0-7.2 (3H, m).

REFERENCE EXAMPLE 13

In the same manner as Reference Example 11, ethyl 2-chloro-2-(3,4-ethylenedioxyphenyl)acetate was obtained as an oil. Yield 90%.

bp. 165°-167° C./0.3 mmHg

NMR (δ ppm, $CDCl_3$): 1.27 (3H, t, J=7 Hz), 4.1-4.4 (2H, m), 4.27 (4H, s), 5.25 (1H, s), 6.8-7.1 (3H, m).

REFERENCE EXAMPLE 14

In the same manner as Reference Example 11, ethyl 2-chloro-2-(4-hexylphenyl)acetate was obtained as an oil.

bp. 152°-155° C./0.5 mmHg

NMR (δ ppm, $CDCl_3$): 0.88 (3H, t, J=7 Hz), 1.26 (3H, t, J=7 Hz), 1.1-1.8 (8H, m), 2.60 (2H, t, J=7 Hz), 4.1-4.4 (2H, m), 5.33 (1H, s), 7.19 (2H, d, J=9 Hz), 7.40 (2H, d, J=9 Hz).

REFERENCE EXAMPLE 15

To a solution of ethyl 2-hydroxy-2-(3,4-dimethoxyphenyl)acetate (19.5 g) in benzene (200 ml) was added phosphorus tribromide (8.18) dropwise at 50° C. and the mixture was stirred at 60° C. for one hour. The reaction mixture was then washed successively with water, saturated aqueous solution of $NaHCO_3$ and water and dried ($MgSO_4$). The benzene was distilled off and the residue was subjected to silica gel chromatography. From the fraction eluted by ethyl acetate-hexane (1:3, v/v), ethyl 2-bromo-2-(3,4-dimethoxyphenyl)acetate (18.5 g, yield 75%) was obtained as an oil.

NMR (δ ppm, $CDCl_3$): 1.27 (3H, t, J=7 Hz), 3.86 (3H, s), 3.89 (3H, s), 4.23 (2H, q, J=7 Hz), 5.31 (1H, s), 6.80 (1H, d, J=8 Hz), 7.0-7.2 (2H, m).

REFERENCE EXAMPLE 16

In acetone (400 ml) was dissolved 4-cyclohexylaniline (50 g) followed by addition of 47% aqueous HBr (147 g). Then, a solution of $NaNO_2$ (21.6 g) in water (30 ml) was added dropwise at 0°-5° C. and the mixture was stirred at 5° C. for an additional 30 minutes. Thereafter, the reaction mixture was warmed to 15° C. and methyl acrylate (147 g) was added. With vigorous stirring, $Cu_2O$ (1 g) was added in small portions, whereupon an exothermic reaction took place to liberate a nitrogen gas. After the evolution of nitrogen gas had subsided, the reaction mixture was further stirred for 2 hours and, then, concentrated. The residue was diluted with water and extracted with ethyl acetate. The ethyl acetate layer was washed with water, dried ($MgSO_4$) and the solvent was distilled off to give methyl 2-bromo-3-(4-cyclohexylphenyl)propionate as a crude oil (91 g, yield 98%).

NMR (δ ppm, $CDCl_3$): 1.2-2.0 (10H, m), 2.5 (1H, m), 3.15 (1H, d.d, J=14 and 7 Hz), 3.43 (1H, d.d, J=14 and 7 Hz), 3.70 (3H, s), 4.37 (1H, t, J=7 Hz), 7.10 (4H, s).

REFERENCE EXAMPLE 17

A solution of ethyl 2-chloro-2-(5,6,7,8-tetrahydro-2-naphthyl)acetate (32 g) in acetone (50 ml) was added to a mixture of thioglycolic acid (14 g), $K_2CO_3$ (52.7 g) and acetone (250 ml). This mixture was refluxed for 5 hours and, concentrated in vacuo. The residue was poured into water and extracted with ether. The aqueous layer was acidified with concentrated hydrochloric acid and extracted with ethyl acetate. The ethyl acetate layer was washed with water, dried ($MgSO_4$) and concentrated. The residue was subjected to silica gel chromatography. From the fraction eluted by chloroform-ethyl acetate-methanol (20:2:1, v/v), ethoxycarbonyl(5,6,7,8-tetrahydro-2-naphthyl)methylthioacetic acid (31.8 g, yield 81%) was obtained as an oil.

NMR (δ ppm, $CDCl_3$): 1.23 (3H, t, J=7 Hz), 1.8 (4H, m), 2.7 (4H, m), 3.07 (1H, d, J=15 Hz), 3.30 (1H, d, J=15 Hz), 4.18 (2H, q, J=7 Hz), 4.79 (1H, s), 6.9-7.2 (3H, m).

REFERENCE EXAMPLE 18

In the same manner as Reference Example 17, ethoxycarbonyl(3,4-dimethoxyphenyl)methylthioacetic acid was obtained as an oil (yield 98%).

NMR (δ ppm, $CDCl_3$): 1.23 (3H, t, J=7 Hz), 3.18 (2H, dd, J=21 and 15 Hz), 3.87 (6H, s), 4.20 (2H, q, J=7 Hz), 4.81 (1H, s), 6.7-7.1 (3H, m), 9.40 (1H, broad).

REFERENCE EXAMPLE 19

In the same manner as Reference Example 17, ethoxycarbonyl(4-cyclohexylphenyl)methylthioacetic acid was obtained as an oil (yield 85%).

NMR (δ ppm, $CDCl_3$): 1.23 (3H, t, J=7 Hz), 1.2-2.0 (8H, m), 2.5 (1H, m), 3.18 (2H, dd, J=21 and 15 Hz), 4.18 (2H, q, J=7 Hz), 4.83 (1H, s), 7.17 (2H, d, J=9 Hz), 7.38 (2H, d, J=9 Hz).

REFERENCE EXAMPLE 20

Triethylamine (46.5 g) was added dropwise to a mixture of thioglycolic acid (20.8g), ethyl 2-chloro-2-(4-hexylphenyl)acetate (58 g) and DMF (250 ml) under ice-cooling. After completion of dropwise addition, the mixture was further stirred for one hour with ice-cooling, and the resulting reaction mixture was poured into water and extracted with ether. The aqueous layer was acidified with concentrated hydrochloric acid and extracted with ethyl acetate. The ethyl acetate layer was washed with water, dried ($MgSO_4$) and concentrated to give ethoxycarbonyl(4-hexylphenyl)methylthioacetic acid as a crude oil (63.5 g, yield 92%).

NMR (δ ppm, $CDCl_3$): 0.83 (3H, t, J=7 Hz), 1.26 (3H, t, J=7 Hz), 1.1-1.8 (8H, m), 2.59 (2H, t, J=7 Hz), 3.11 (1H, d, J=15 Hz), 3.30 (1H, d, J=15 Hz), 4.1-4.4 (2H, m), 4.84 (1H, s), 7.26 (2H, d, J=9 Hz), 7.35 (2H, d, J=9 Hz).

REFERENCE EXAMPLE 21

In the same manner as Reference Example 20, methoxycarbonylphenylmethylthioacetic acid was obtained as an oil (yield 98%).

NMR (δ ppm, $CDCl_3$): 3.11 (1H, d, J=15 Hz) 3.31 (1H d J=15 Hz), 3.75 (3H, s), 4.90 (1H, s), 7.3-7.5 (5H, m).

REFERENCE EXAMPLE 22

In the same manner as Reference Example 20, methoxycarbonyl(4-chlorophenyl)methylthioacetic acid was obtained as an oil (yield 87%).

NMR (δ ppm, $CDCl_3$): 3.03 (1H, d, J=15 Hz), 3.35 (1H, d, J=15 Hz), 3.67 (3H, s), 4.81 (1H, s), 7.1-7.5 (4H, m).

REFERENCE EXAMPLE 23

In the same manner as Reference Example 20, ethoxycarbonyl(3,4-ethylenedioxyphenyl)methylthioacetic acid was obtained as an oil (yield 97%).

NMR (δ ppm, $CDCl_3$): 1.26 (3H, t, J=7 Hz), 3.13 (1H, d, J=15 Hz), 3.30 (1H, d, J=15 Hz), 4.1-4.4 (2H, m), 4.26 (4H, s), 4.78 (1H, s), 6.8-7.1 (3H, m).

REFERENCE EXAMPLE 24

In the same manner as Reference Example 20, 2-[ethoxycarbonyl(4-cyclohexylphenyl)methylthio]propionic acid was obtained as an oil (yield 89%).

NMR (δ ppm, $CDCl_3$): 1.1-2.0 (16H, m), 2.5 (1H, m), 3.49 (2H, q, J=7 Hz), 4.1-4.4 (2H, m), 4.88 (1H, s), 7.1-7.4 (4H, m).

In the same manner as Reference Example 20, methyl 2-carboxymethylthio-3-(4-cyclohexylphenyl)propionate was obtained as an oil (yield 84%).

NMR (δ ppm, $CDCl_3$): 1.2–1.9 (10H, m), 2.5 (1H, m), 2.96 (1H, d.d, J=15 and 7 Hz), 3.35 (1H, d, J=16 Hz), 3.49 (1H, d, J=16 Hz), 3.52 (1H, d.d, J=15 and 7 Hz), 3.68 (3H, s), 3.6–3.8 (1H, m), 7.12 (4H, s).

REFERENCE EXAMPLES 26 THROUGH 41

In substantially the same manner as Reference Example 1, the compound shown in Table 5 were obtained.

TABLE 5

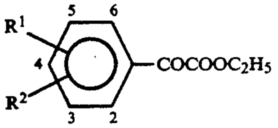

| Reference Example No. | $R^1$, $R^2$ | Yield (%) | mp (°C./mmHg) |
|---|---|---|---|
| 26 | H, 4-$CH_3$ | 85 | 112–115/0.4 |
| 27 | H, 4-$(CH_3)_2CH$— | 75 | 124–127/0.4 |
| 28 | H, 4-$(CH_3)_3C$— | 82 | 140–142/0.7 |
| 29 | H, 4-$C_2H_5C(CH_3)_2$— | 75 | 145–148/0.4 |
| 30 | H, 4-$(CH_3)_3CCH_2$— | 59 | 150–153/1.0 |
| 31 | H, 4— 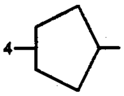 | 84 | 153–155/0.5 |
| 32 | H, 4— 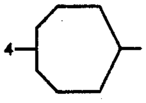 | 78 | 170–172/0.5 |

TABLE 5-continued

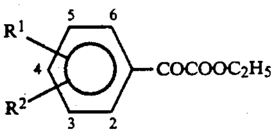

| Reference Example No. | $R^1$, $R^2$ | Yield (%) | mp (°C./mmHg) |
|---|---|---|---|
| 33 | H, 4— 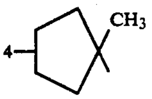 | 69 | 160–162/1.0 |
| 34 | H, 4— 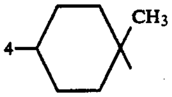 | 75 | 172–174/0.8 |
| 35 | 2-$CH_3$, 5-$CH_3$ | 85 | 116–118/0.7 |
| 36 | 2-$CH_3$, 4-$CH_3$ | 85 | 58–59° C. (Recrystallization hexane) |
| 37 | 3-$CH_3$, 4-$CH_3$ | 89 | 125–127/0.8 |
| 38 | 3-$C_2H_5$, 4-$C_2H_5$ | 90 | 133–135/2.0 |
| 39 | 2-$(CH_3)_2CH$—, 4-$(CH_3)_2CH$— | 64 | 130–132/0.4 |
| 40 | 3,4-$(CH_2)_3$— | 75 | 138–141/0.3 |
| 41 | 3,4-$(CH_2)_5$— | 70 | 153–155/0.2 |

REFERENCE EXAMPLES 42 THROUGH 57

In substantially the same manner as Reference Example 6, the compounds shown in Table 6 were obtained.

TABLE 6

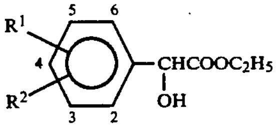

| Reference Example No. | $R^1$, $R^2$ | Yield (%) | mp (°C.) Recrystallization solvent | NMR(δ ppm $CDCl_3$) |
|---|---|---|---|---|
| 42 | H, 4-$CH_3$ | 76 | 75–76 (Ether-hexane) | |
| 43 | H, 4-$(CH_3)_2CH$— | 96 | Oil | 1.24(6H, d, J=7), 1.25(3H, t, J=7), 2.91(1H, m), 3.40(1H, d, J=6), 4.1–4.4(2H, m), 5.13(1H, d, J=6), 7.22 (2H, d, J=9), 7.34(2H, d, J=9) |
| 44 | H, 4-$(CH_3)_3C$— | 96 | Oil | 1.27(3H, t, J=7), 1.29(9H, s), 3.35 (1H, braod), 4.0–4.5(2H, m), 5.13 (1H, s), 7.34(4H, s) |
| 45 | H, 4-$C_2H_5C(CH_3)_2$— | 97 | Oil | 0.66(3H, t, J=7), 1.21(3H, t, J=7), 1.26(6H, s), 1.68(2H, q, J=7), 3.35 (1H, braod), 4.0–4.4(2H, m), 7.29 (4H, s) |
| 46 | H, 4-$(CH_3)_3C.CH_2$— | 97 | Oil | 0.89(9H, s), 1.22(3H, t, J=7), 2.46 (2H, s), 3.4(1H, braod), 4.0–4.4 (2H, m), 5.11(1H, s), 7.10(2H, d, J=9), 7.32(2H, d, J=9) |
| 47 | H, 4— 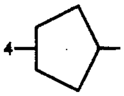 | 98 | Oil | 1.21(3H, t, J=7), 1.4–2.2(8H, m), 2.95(1H, m), 3.47(1H, brs), 4.0–4.4(2H, m), 5.11(1H, s), 7.19(2H, d, J=9), 7.31(2H, d, J=9) |
| 48 | H, 4— 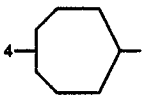 | 96 | 79–80 (Hexane) | |

TABLE 6-continued

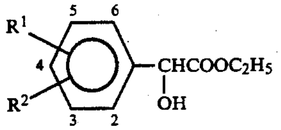

| Reference Example No. | $R^1$, $R^2$ | Yield (%) | mp (°C.) Recrystallization solvent | NMR(δ ppm $CDCl_3$) |
|---|---|---|---|---|
| 49 | H, 4— 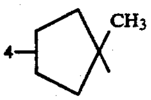 | 99 | Oil | 1.23(3H, t, J=7), 1.24(3H, s), 1.5-2.1(8H, m), 3.4(1H, br), 4.0-4.4 (2H, m), 5.12(1H, s), 7.32(4H, s) |
| 50 | H, 4— 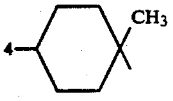 | 98 | Oil | 1.16(3H, s), 1.22(3H, t, J=7), 1.3-2.1(10H, m), 3.45(1H, br), 4.1-4.4 (2H, m), 5.14(1H, brs), 7.37(4H, s) |
| 51 | 2-$CH_3$, 5-$CH_3$ | 96 | Oil | 1.17(3H, t, J=7), 2.26(3H, s), 2.35 (3H, s), 3.48(1H, d, J=5), 4.0-4.4 (2H, m), 5.27(1H, d, J=5), 6.9-7.1 (4H, m) |
| 52 | 2-$CH_3$, 4-$CH_3$ | 97 | Oil | 1.18(3H, t, J=7), 2.27(3H, s), 2.36 (3H, s), 3.41(1H, d, J=5), 4.0-4.4 (2H, m), 5.28(1H, d, J=5), 6.95(2H, d, J=9), 7.17(2H, d, J=9) |
| 53 | 3-$CH_3$, 4-$CH_3$ | 95 | Oil | 1.17(3H, t, J=7), 2.26(6H, s), 3.47 (1H, d, J=5), 4.0-4.4(2H, m), 5.03 (1H, d, J=5), 7.0-7.2(4H, m) |
| 54 | 3-$C_2H_5$, 4-$C_2H_5$ | 94 | Oil | 1.16(6H, t, J=7), 1.21(3H, t, J=7), 2.63(4H, q, J=7), 3.1(1H, br), 4.0-4.4(2H, m), 5.09(1H, s), 7.1-7.3 (4H, m) |
| 55 | 2-$(CH_3)_2CH$—, 4-$(CH_3)_2CH$— | quant. | Oil | 1.1-1.4(15H, m), 2.7-3.1(1H, m), 3.1-3.5(2H, m), 4.0-4.4(2H, m), 5.41(1H, s), 6.9-7.3(4H, m) |
| 56 | 3,4-$(CH_2)_3$— | 93 | Oil | 1.17(3H, t, J=7), 1.8-2.4(2H, m), 2.83(2H, t, J=7), 3.80(1H, d, J=6), 4.13(2H, q, J=7), 5.05(1H, d, J=6), 7.1-7.4(3H, m) |
| 57 | 3,4-$(CH_2)_5$— | quant. | Oil | 1.20(3H, t, J=7), 1.7(6H, m), 2.6-2.9(4H, m), 3.57(1H, d, J=6), 4.18 (2H, q, J=7), 5.0(1H, d, J=6), 7.0 (3H, m) |

REFERENCE EXAMPLES 58 THROUGH 73

In substantially the same manner as Reference Example 11, the compounds shown in Table 7 were obtained.

TABLE 7

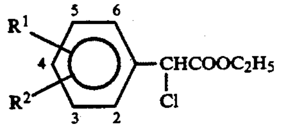

| Reference Example No. | $R^1$, $R^2$ | Yield (%) | mp (°C./mmHg) |
|---|---|---|---|
| 58 | H, 4-$CH_3$ | quant. | Note 1) |
| 59 | H, 4-$(CH_3)_2CH$— | 82 | 116-118/0.5 |
| 60 | H, 4-$(CH_3)_3C$— | 91 | 135-138/0.5 |
| 61 | H, 4-$C_2H_5C(CH_3)_2$— | 92 | 135-138/0.5 |
| 62 | H, 4-$(CH_3)_3C.CH_2$— | 99 | 138-140/1.5 |
| 63 | H, 4— 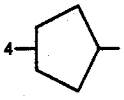 | 89 | 152-154/0.6 |

TABLE 7-continued

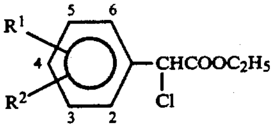

| Reference Example No. | $R^1$, $R^2$ | Yield (%) | mp (°C./mmHg) |
|---|---|---|---|
| 64 | H, 4— 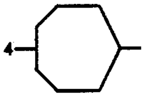 | 98 | Note 2) |
| 65 | H, 4— 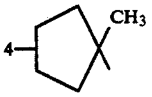 | 91 | 158-160/1.0 |
| 66 | H, 4— 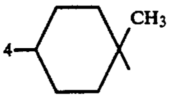 | 85 | 163-165/0.7 |
| 67 | 2-$CH_3$, 5-$CH_3$ | 88 | 108-110/0.5 |

TABLE 7-continued

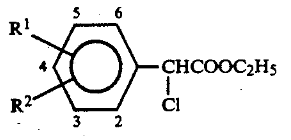

| Reference Example No. | $R^1$, $R^2$ | Yield (%) | mp (°C./mmHg) |
|---|---|---|---|
| 68 | 2-$CH_3$, 4-$CH_3$ | 93 | 115-118/0.5 |
| 69 | 3-$CH_3$, 4-$CH_3$ | 90 | 118-120/0.7 |
| 70 | 3-$C_2H_5$, 4-$C_2H_5$ | quant. | Note 3) |
| 71 | 2-$(CH_3)_2CH$—, 4-$(CH_3)_2CH$— | 95 | 129-132/0.5 |
| 72 | 3,4-$(CH_2)_3$— | 92 | 128-132/0.3 |

TABLE 7-continued

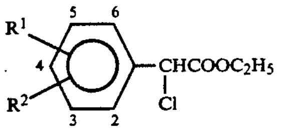

| Reference Example No. | $R^1$, $R^2$ | Yield (%) | mp (°C./mmHg) |
|---|---|---|---|
| 73 | 3,4-$(CH_2)_5$— | 89 | 145-148/0.2 |

Note 1) NMR(δ ppm, $CDCl_3$): 1.26(3H, t, J=7), 2.36(3H, s), 4.1-4.3(2H, m), 5.32(1H, s), 7.19(2H, d, J=9), 7.38(2H, d, J=9)
Note 2) NMR(δ ppm, $CDCl_3$): 1.24(3H, t, J=7), 1.3-2.1(12H, m), 2.7(1H, m), 4.20(2H, q, J=7), 5.30(1H, s), 7.18(2H, d, J=9), 7.40(2H, d, J=9)
Note 3) NMR(δ ppm, $CDCl_3$): 1.20(6H, t, J=7), 1.26(3H, t, J=7), 2.66(4H, q, J=7), 4.23(2H, q, J=7), 5.31(1H, s), 7.1-7.3(3H, m)

REFERENCE EXAMPLES 74 THROUGH 90

In substantially the same manner as Reference Example 20, the compounds shown in Table 8 were obtained.

TABLE 8

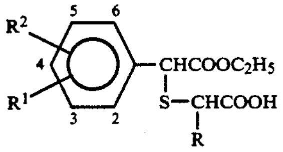

| Reference Example No. | $R^1$, $R^2$ | R | Yield (%) | NMR(δppm $CDCl_3$) |
|---|---|---|---|---|
| 74 | H, 4-$CH_3$ | H | 90 | 1.24(3H, t, J=7), 2.34(3H, s), 3.09(1H, d, J=15), 3.29(1H, d, J=15), 4.1-4.3(2H, m), 4.85 (1H, s), 7.17(2H, d, J=8), 7.33(2H, d, J=8) |
| 75 | H, 4-$(CH_3)_2CH$— | H | 90 | 1.26(6H, d, J=7), 1.26(3H, t, J=7), 2.90(1H, m), 3.11(1H, d, J=16), 3.31(1H, d, J=16), 4.1-4.3(2H, m), 4.86(1H, s), 7.21(2H, d, J=8), 7.38(2H, d, J=8) |
| 76 | H, 4-$(CH_3)_3C$— | H | 86 | 1.24(3H, t, J=7), 1.29(9H, s), 3.08(1H, d, J=16), 3.34(1H, d, J=16), 4.20(2H, q, J=7), 4.84(1H, s), 7.36(4H, s), 9.45(1H, broad) |
| 77 | H, 4-$C_2H_5C(CH_3)_2$— | H | 93 | 0.66(3H, t, J=7), 1.24(3H, t, J=7), 1.29(6H, s), 1.64(2H, (2H, q, J=7), 3.05(1H, d, J=16), 3.30(1H, d, J=16), 4.19(2H, q, J=7), 4.83(1H, s), 7.28(2H, d, J=8), 7.42(2H, d, J=8) |
| 78 | H, 4-$(CH_3)_3C.CH_2$— | H | 89 | 0.90(9H, s), 1.26(3H, t, J=7), 2.48(2H, s), 3.12(1H, d, J=16), 3.31(1H, d, J=16), 4.1-4.3 (2H, m)4.85(1H, s), 7.12(2H, d, J=8), 7.34 (2H, d, J=8) |
| 79 | H, 4— 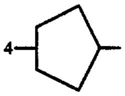 | H | 86 | 1.25(3H, t, J=7), 1.4-2.1(8H, m), 2.9(1H, m), 3.07(1H, d, J=15), 3.30(1H, d, J=15)4.17 (2H, q, J=7), 4.82(1H, s), 7.19(2H, d, J=9), 7.38(2H, d, J=9), 10.19(1H, br s) |
| 80 | H, 4— 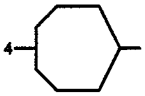 | H | 88 | 1.23(3H, t, J=7), 1.3-2.1(12H, m), 2.7(1H, m), 3.05(1H, d, J=16), 3.30(1H, d, J=16), 4.18 (2H, q, J=7), 4.81(1H, s), 7.15(2H, d, J=9), 7.35(2H, d, J=9), 8.85(1H, br s) |
| 81 | H, 4— 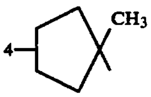 | H | 95 | 1.22(3H, t, J=7), 1.24(3H, s), 1.4-2.1(8H, m)3.05(1H, d, J=16), 3.32(1H, d, J=16), 4.18 (2H, q, J=7), 4.83(1H, s), 7.19(2H, q, J=9), 7.35(2H, d, J=9) |
| 82 | H, 4— 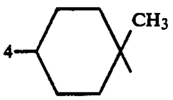 | H | 92 | 1.16(3H, t, J=7), 1.25(3H, s), 1.3-2.1(10H, m), 3.08(1H, d, J=16), 3.33(1H, d, J=16), 4.20 (2H, q, J=7), 4.83(1H, s), 7.1-7.5(4H, m) |
| 83 | 2-$CH_3$, 5-$CH_3$ | H | 96 | 1.22(3H, t, J=7), 2.29(3H, s), 2.36(3H, s), 3.10(1H, d, J=16), 3.36(1H, d, J=16), 4.19(2 |

TABLE 8-continued

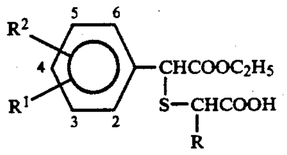

| Reference Example No. | $R^1$, $R^2$ | R | Yield (%) | NMR(δppm $CDCl_3$) |
|---|---|---|---|---|
| | | | | H, q, J=7), 5.08(1H, s), 7.03(2H, s), 7.27(1H, s), 9.40(1H, br s) |
| 84 | 2-$CH_3$, 4-$CH_3$ | H | 97 | 1.21(3H, t, J=7), 2.27(3H, s), 2.36(3H, s), 3.10(1H, d, J=16), 3.36(1H, d, J=16), 4.18 (2H, q, J=7), 5.08(1H, s), 7.0(2H, m), 7.33 (1H, d, J=8), 10.09(1H, br s) |
| 85 | 3-$C_2H_5$, 4-$C_2H_5$ | H | 90 | 1.19(6H, t, J=7), 1.23(3H, t, J=7), 2.63(4H, q, J=7)3.08(1H, d, J=16), 3.32(1H, d, J=16), 4.20(2H, q, J=7), 4.81(1H, s), 7.1-7.3(3H, m), 8.07(1H, br s) |
| 86 | 2-$(CH_3)_2CH$—, 4-$(CH_3)_2CH$— | H | 84 | 1.21(6H, d, J=7), 1.23(3H, t, J=7), 1.27(6H, d, J=7), 2.7-3.1(2H, m), 3.12(1H, d, J=16), 3.40(1H, d, J=16), 4.18(2H, q, J=7), 5.19(1H, s), 6.9-7.2(2H, m), 7.37(1H, d, J=8), 9.35(1 H, br s) |
| 87 | 3,4-$(CH_2)_3$— | H | 94 | 1.24(3H, t, J=7), 1.9-2.3(2H, m), 2.88(4H, t, J=7), 3.12(1H, d, J=16), 3.32(1H, d, J=16), 4.20(2H, q, J=7), 4.84(1H, s), 7.1-7.4(3H, m), 8.60(1H, br s) |
| 88 | 3,4-$(CH_2)_3$— | $CH_3$ | 83 | 1.24(3H×2/5, t, J=7), 1.26(3H×3/5, t, J=7), 1.38(3H×2/5, t, J=7), 1.44(3H×3/5, t, J=7), 2.0-2.2(2H, m), 2.8-3.0(4H, m), 3.19(1H× 2/5, q, J=7), 3.58(1H×3/5, q, J=7), 4.1-4.3 (2H, m), 4.88(1H×2/5, s), 4.89(1H×3/5, s), 7.1-7.4(3H, m) |
| 89 | 3,4-$(CH_2)_4$— | $CH_3$ | 72 | 1.1-1.3(3H, m), 1.38(3H×2/5, t, J=7), 1.44 (3H×3/5, t, J=7), 1.8(4H, m), 2.75(4H, br s), 3.19(1H×2/5, q, J=7), 3.58(1H×3/5, q, J=7), 4.1-4.4(2H, m), 4.83(1H×2/5, s), 4.85(1H× 3/5, s), 7.0-7.3(3H, m) |
| 90 | 3,4-$(CH_2)_5$— | H | quant. | 1.24(3H, t, J=7), 1.4-2.0(6H, m), 2.80(4H, m), 3.07(1H, d, J=16), 3.33(1H, d, J=16), 4.19 (2H, q, J=7), 4.79(1H, s), 7.0-7.3(3H, m), 7.90(1H, br s) |

REFERENCE EXAMPLE 91

Potassium thioacetate ($CH_3COSK$, 8.31 g) was added in small portions to a solution of ethyl 2-chloro-2-(3,4-dimethylphenyl)acetate (15 g) in DMF (80 ml). The mixture was stirred at room temperature for 2 hours, at the end of which time it was poured into water and extracted with ethyl acetate. The ethyl acetate layer was washed with water, dried ($MgSO_4$) and the solvent was distilled off to give ethyl 2-acetylthio-2-(3,4-dimethylphenyl)acetate (16.5 g, 94%) as an oil.

NMR (δ ppm, $CDCl_3$): 1.22 (3H, t, J=7 Hz), 2.21 (6H, s), 2.30 (3H, s), 4.0-4.35 (2H, m), 5.2 (1H, s), 7.05-7.2 (3H, m).

REFERENCE EXAMPLE 92

Morpholine (21.6 g) was added dropwise to a solution of ethyl 2-acetylthio-2-(3,4-dimethylphenyl)acetate (16.5 g) in ethanol (80 ml) at room temperature and the mixture was further stirred at the same temperature for 2 hours. The reaction mixture was then poured into water, acidified with 2N-HCl and extracted with ethyl acetate. The ethyl acetate layer was washed with water, dried ($MgSO_4$) and the solvent was distilled off. Finally the residue was subjected to silica gel column chromatography with chloroform-hexane (1:3, v/v) to give ethyl 2-thio-2-(3,4-dimethylphenyl)acetate (8.8 g, 63%) as an oil.

NMR (δ ppm, in $CDCl_3$): 1.23 (3H, t, J=7 Hz), 2.23 (6H, broad s), 2.53 (1H, d, J=7.5 Hz), 4.17 (2H, q, J=7 Hz), 4.60 (1H, d, J=7.5 Hz), 7.0-7.3 (3H, m).

REFERENCE EXAMPLE 93

A mixture of ethyl 2-thio-2-(3,4-dimethylphenyl)acetate (4.5 g), 2-bromobutyric acid (3.3 g), potassium carbonate (5.5 g) and DMF (30 ml) was stirred at room temperature for 1 hour, after which it was poured into water and extracted with ether. The aqueous layer was acidified with concentrated hydrochloric acid and extracted with ether. The ether layer was washed with water, dried ($MgSO_4$) and the solvent was distilled off to give 2-[ethoxycarbonyl(3,4-dimethylphenyl)methylthio]butyric acid (5.5 g, 89%) as an oil.

NMR (δ ppm, $CDCl_3$): 0.9-1.1 (3H, m), 1.1-1.3 (3H, m), 1.6-2.0 (2H, m), 2.25 (6H, s), 2.97 (1H ×½, t, J=7 Hz), 3.38 (1H ×½, t, J=7 Hz), 4.1-4.3 (2H, m), 4.78 (1H ×½, s), 4.80 (1H ×½, s), 7.0-7.3 (3H, m)

REFERENCE EXAMPLES 94 THROUGH 97

In substantially the same manner as Reference Example 93, the compounds shown in Table 9 were obtained as oils.

TABLE 9

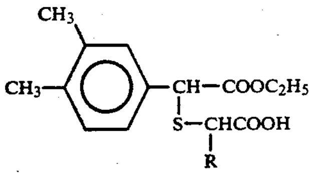

| Reference Example No. | R | Yield (%) | NMR(δppm, $CDCl_3$) |
|---|---|---|---|
| 94 | H | 90 | 1.23(3H, t, J=7), 2.25(6H, s), 3.0 5(1H, d, J=16), 3.29(1H, d, J=16), 4.18(2H, q, J=7), 5.13(1H, s),7.0–7.3(3H, m), 9.98(1H, br s) |
| 95 | $CH_3$ | 90 | 1.23(3H×3/5, t, J=7), 1.27(3H×2/5, t, J=7), 1.37(3H×3/5, t, J=7), 1.44(3H×2/5, t, J=7), 2.24(6H, s), 3.16(1H×2/5, q, J=7), 3.59(1H×3/5, q, J=7), 4.1–4.3(2H, m), 4.86 (1H, s), 7.1–7.3(3H, m) |
| 96 | $C_3H_7$ | 88 | 0.75–1.05(3H, m), 1.15–1.50(3H, m), 1.3–2.0(4H, m), 2.24(6H, s), 3.04 (1H×½, t, J=7), 3.48(1H×½, t, J=7), 4.1–4.3(2H, m), 4.79(1H×½, s), 4.80(1H×½, s), 7.05–7.3 (3H, m) |
| 97 | 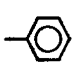 | 88 | 1.20(3H×½, t, J=7), 1.21(3H×½, t, J=7), 2.22(6H×½, s), 2.23 (6H×½, s), 4.0–4.3(2H, m), 4.49 (1H, s), 4.52(1H×½, s), 4.55(1H×½, s), 7.0–7.5(8H, m) |

WORKING EXAMPLES

Example 1

In THF (400 ml) was dissolved methoxycarbonyl(4-chlorophenyl)methylthioacetic acid (71 g), followed by addition of oxalyl chloride (39 g) and, then, DMF (5 drops). The mixture was allowed to stand at room temperature overnight, concentrated and the residue was dissolved in dichloromethane (100 ml). The solution was added dropwise to a suspension of aluminum chloride (69 g) in dichloromethane (400 ml) with ice-cooling. After completion of dropwise addition, the reaction mixture was further stirred at room temperature for 3 hours, after which it was poured into ice-water, and the organic layer was separated. The aqueous layer was extracted with chloroform. The combined organic layer was washed with water and dried ($MgSO_4$). The solvent was then distilled off and the residue was subjected to silica gel chromatography. From the fraction eluted by ether-hexane (1:1, v/v), methyl 6-chloro-3,4-dihydro-1H-2-benzothiopyran-4-one-1-carboxylate was obtained as crystals (27 g, yield 40%). Recrystallization from ethyl acetate-hexane gave colorless plates.

mp. 118°–119° C.

Elemental analysis: $C_{11}H_9O_3SCl$

Calcd C, 51.47; H, 3.53.

Found : C, 51.40; H, 3.5.

In methanol (100 ml) was suspended methyl 6-chloro-3,4-dihydro-1H-2-benzothiopyran-4-one-1-carboxylate (21.5 g) followed by addition of 2N-KOH (70 ml). The mixture was stirred at room temperature for one hour. The resulting reaction mixture was poured into water, acidified and extracted with ethyl acetate. The ethyl acetate layer was washed with water, dried ($MgSO_4$) and the solvent was distilled off to give 6-chloro-3,4-dihydro-1H-2-benzothiopyran-4-one-1-carboxylic acid (18.8 g, yield 93%). Recrystallization from ethyl acetate gave colorless prisms.

mp. 220°–221° C.

Elemental analysis: $C_{10}H_7O_3SCl$

Calcd C, 49.49; H, 2.91.

Found : C, 49.51: H, 2.91.

EXAMPMLE 2

In ether (500 ml) was dissolved ethoxycarbonyl(4-hexylphenyl)methylthioacetic acid (63 g), followed by addition of thionyl chloride (33 g) and, then, pyridine (5 drops). The mixture was refluxed for 30 minutes and then, concentrated, and the residue was dissolved in dichloromethane (50 ml). This solution was added dropwise to a suspension of aluminum chloride (50 g) in dichloromethane (350 ml) with ice-cooling. After completion of dropwise addition, the reaction mixture was further stirred with ice cooling for 3 hours and, then, poured into ice-water. The organic layer was separated and the aqueous layer was extracted with chloroform. The organic layers were combined, washed with water and dried ($MgSO_4$). The solvent was then distilled off and the residue was subjected to silica gel chromatography. From the fraction eluted by ether-hexane (1:2, v/v), ethyl 6-hexyl-3,4-dihydro-1H-2-benzothiopyran-4-one-1-carboxylate was obtained as an oil (42 g, yield 70%).

NMR (δ ppm, $CDCl_3$): 0.83 (3H, t, J=7 Hz), 1.2–1.7 (8H, m), 1.30 (3H, t, J=7 Hz), 2.64 (2H, t, J=7 Hz), 3.27 (1H, d.d, J=16 and 1 Hz), 4.24 (2H, q, J=7 Hz), 4.27 (1H, d.d, J=16 and 1 Hz), 4.41 (1H, s), 7.1–7.4 (2H, m), 7.94 (1H, d, J=2 Hz).

In methanol (150 ml) was suspended ethyl 6-hexyl-3,4-dihydro-1H-2-benzothiopyran-4-one-1-carboxylate (41 g) followed by addition of 2N-KOH (150 ml). The mixture was stirred at room temperature for one hour. The reaction mixture was poured in water, acidified and extracted with ethyl acetate. The ethyl acetate layer was washed with water, dried ($MgSO_4$) and the solvent was distilled off to give 6-hexyl-3,4-dihydro-1H-2-benzothiopyran-4-one-1-carboxylic acid (27.5 g, yield 74%). Recrystallization from ether-hexane gave colorless plates.

mp. 66°–67° C.

Elemental analysis: $C_{16}H_{20}O_3S$

Calcd C, 65.72; H, 6.89.

Found : C, 65.73; H, 6.90.

EXAMPLE 3

In the same manner as Example 2, ethyl 6-cyclohexyl-3,4-dihydro-1H-2-benzothiopyran-4-one-1-carboxylate was obtained. Yield 69%. Recrystallization from hexane gave colorless prisms.

m.p. 51°–5220 C. Elemental analysis: $C_{18}H_{22}O_3S$

Calcd. C, 67.89; H, 6.96.

Found: C, 68.08; H, 7.01.

EXAMPLE 3

In methanol (200 ml) was suspended ethyl 6-cyclohexyl-3,4-dihydro-1H-2-benzothiopyran-4-one-1-carboxylate (52 g) followed by addition of 2N-KOH (100 ml). The mixture was stirred at room temperature for one hour, poured into water, acidified and extracted with ethyl acetate. The ethyl acetate layer was washed with water, dried ($MgSO_4$) and the solvent was distilled off to give 6-cyclohexyl-3,4-dihydro-1H-2-benzothiopyran-4-one-1-carboxylic acid (33 g, yield 73%). Recrystallization from ethyl acetate-hexane gave colorless plates.

m.p. 171°-172° C.

Elemental analysis: $C_{16}H_{18}O_3S$

Calcd.: C, 66.18; H, 6.25.

Found : C, 66.16; H, 6.28.

EXAMPLE 4

In the same manner as Example 2, ethyl 3,4,6,7,8,9-hexahydro-1H-naphto[2,3-c]thiopyran-4-one-1-carboxylate was obtained as an oil. Yield 81%.

NMR (δ ppm, $CDCl_3$): 1.27 (3H, t, J=7 Hz), 1.75 (4H, m), 2.75 (4H, m), 3.19 (1H, d, J=16 Hz), 4.18 (1H, d, J=16 Hz), 4.19 (2H, q, J=7 Hz), 4.31 (1H, s), 6.87 (1H, s), 7.81 (1H, s).

In methanol (20 ml) was suspended ethyl 3,4,6,7,8,9-hexahydro-1H-naphto[2,3-c]thiopyran-4-one-1-carboxylate (2.9 g) followed by addition of 2N-KOH (10 ml). The mixture was stirred at room temperature for one hour, poured into water, acidified and extracted with ethyl acetate. The ethyl acetate layer was washed with water, dried ($MgSO_4$) and the solvent was distilled off to give 3,4,6,7,8,9-hexahydro-1H-naphto[2,3-c]thiopyran-4-one-1-carboxylic acid (2.3 g, yield 89%). Recrystallization from ethyl acetate gave colorless prisms. m.p. 204°-205° C.

Elemental analysis: $C_{14}H_{14}O_3S$

Calcd.: C, 64.10; H, 5.38.

Found : C, 64.38; H, 5.40.

EXAMPLE 5

In the same manner as Example 2, ethyl 6,7-ethylenedioxy-3,4-dihydro-1H-2-benzothiopyran-4-one-1-carboxylate was obtained as an oil. Yield 73%.

NMR (δ ppm, $CDCl_3$): 1.31 (3H, t, J=7 Hz), 3.21 (1H, d.d, J=16 and 1 Hz), 4.15-4.35 (6H, m), 6.72 (1H, s), 7.66 (1H, s).

In ethanol (200 ml) was suspended ethyl 6,7-ethylenedioxy-3,4-dihydro-1H-2-benzothiopyran-4-one-1-carboxylate (55 g) followed by addition of 2N-NaOH (200 ml). The mixture was stirred at room temperature for one hour. The reaction mixture was poured into water, acidified and extracted with ethyl acetate. The ethyl acetate layer was washed with water, dried ($MgSO_4$) and the solvent was distilled off to give 6,7-ethylenedioxy-3,4-dihydro-1H-2-benzothiopyran-4-one-1-carboxylic acid (32.5 g, yield (65%). Recrystallization from ethyl acetate gave colorless prisms.

mp. 207°-208° C.

Elemental analysis: $C_{12}H_{10}O_5S$

Calcd C, 54.13; H, 3.79.

Found : C, 54.37; H, 3.82.

EXAMPLE 6

In the same manner as Example 2, methyl 3,4-dihydro1H-2-benzothiopyran-4-one-1-carboxylate was obtained as an oil. Yield 73%.

NMR (δ ppm, $CDCl_3$): 3.25 (1H, d, J=24 Hz), 3.77 (3H, s), 4.26 (1H, d, J=24 Hz), 4.47 (1H, s), 7.0-7.5 (5H, m), 7.9-8.1 (1H, m).

In methanol (150 ml) was suspended methyl 3,4-dihydro-1H-2-benzothiopyran-4-one-1-carboxylate (32 g) followed by addition of 2N-KOH (150 ml). The mixture was stirred at room temperature for one hour, poured into water, acidified and extracted with ethyl acetate. The ethyl acetate layer was washed with water, dried ($MgSO_4$) and the solvent was distilled off to give 3,4-dihydro-1H-2-benzothiopy:ran-4-one-1-carboxylic acid (22 g, yield 73%). Recrystallization from ethyl acetate-hexane gave colorless prisms.

mp. 124°-125° C.

Elemental analysis: $C_{10}H_6O_3S$

Calcd.: C, 57.68; H, 3.87.

Found : C, 57.88; H, 3.9.

EXAMPLE 7

In the same manner as Example 2, ethyl 6,7-dimethoxy-3,4-dihydro-1H-2-benzothiopyran-4-one-1-carboxylate was obtained. Yield 69%. Recrystallization from methanol gave colorless rods.

m.p. 82°-83° C.

Elemental analysis: $C_{14}H_{16}O_5S$

Calcd C, 56.74; H, 5.44.

Found : C, 56.95; H, 5.44.

In methanol (20 ml) was suspended ethyl 6,7-dimethoxy-3,4-dihydro-1H-2-benzothiopyran-4-one-1-carboxylate (6 g) followed by addition of 2N-KOH (15 ml) and the mixture was stirred at room temperature for one hour. The reaction mixture was then poured into water, acidified and extracted with ethyl acetate. The ethyl acetate layer was washed with water, dried ($MgSO_4$) and the solvent was distilled off to give 6,7-dimethoxy-3,4-dihydro-1H-2-benzothiopyran-4-one-1-carboxylic acid (4.4 g, yield 82%). Recrystallization from methanol gave colorless prisms. m.p. 212°-213° C.

Elemental analysis: $C_{12}H_{12}O_5S$

Calcd.: C, 53.72; H, 4.5.

Found: C, 53.76; H, 4.6.

EXAMPLE 8

In the same manner as Example 2, methyl 7-cyclohexyl-1,2,4,5-tetrahydro-3-benzothiepin-5-one-2-carboxylate was obtained Yield 76%.

NMR (δ ppm, $CDCl_3$): 1.2-2.0 (10H, m), 2.55 (1H, m), 3.21 (1H, d.d, J=14 and 5 Hz), 3.4 (1H, m), 3.41 (1H, d, J=18 Hz), 3.63 (1H, d.d, J=14 and 5 Hz), 3.81 (3H, s), 4.00 (1H, d, J=18 Hz), 7.15 (1H, d, J=8 Hz), 7.36 (1H, d.d, J=8 and 2 Hz), 7.77 (1H, d, J=2 Hz).

In methanol (150 ml) was suspended methyl 7-cyclohexyl-1,2,4,5-tetrahydro-3-benzothiepin-5-one-2-carboxylate (40 g) followed by addition of 2N-KOH (100 ml), and the mixture was stirred at room temperature for one hour. The reaction mixture was then poured into water, acidified and extracted with etyl acetate. The ethyl acetate layer was washed with water, dried ($MgSO_4$) and the solvent was distilled off to give 7-cyclohexyl-1,2,4,5-tetrahydro-3-benzothiepin-5-one-2-carboxylic acid (27.5 g, yield 72%). Recrystallization from ethyl acetate gave colorless plates.

m.p. 210°-211° C.

Elemental analysis: $C_{17}H_{20}O_3S$

Calcd.: C, 67.08; H, 6.62.

Found : C, 67.25; H, 6.63.

EXAMPLE 9

In the same manner as Example 2, ethyl 6-cyclohexyl-t-3-methyl-3,4-dihydro-1H-2-benzothiopyran-4-one-r-1-carboxylate was obtained. Yield 80%.

NMR (δ ppm, $CDCl_3$): 1.32 (3H, t, J=7 Hz), 1.45 (3H, d, J=7 Hz), 1.2-1.9 (10H, m), 2.55 (1H, m), 4.26 (2H, q, J=7 Hz), 4.43 (1H, q, J=7 Hz), 4.43 (1H, s), 7.12 (1H, d, J=8 Hz), 7.36 (1H, d.d, J=8 and 2 Hz), 7.91 (1H, d, J=2 Hz).

In methanol (50 ml) was suspended ethyl 6-cyclohexyl-3-methyl-3,4-dihydro-1H-2-benzothiopyran-4-one-1- carboxylate (11.5 g) followed by addition of 2N-KOH (40 ml), and the mixture was stirred at room temperature for one hour. The reaction mixture was then poured in water, acidified and extracted with ethyl acetate. The ethyl acetate layer was washed with water, dried ($MgSO_4$) and the solvent was distilled off to give 6-cyclohexyl-t-3-methyl-3,4-dihydro1H-2-benzothiopyran-4-one-r-1-carboxylic acid (7.4 g, yield 70%). Recrystallization from ethyl acetate gave colorless plates.

mp. 185°-186° C.

Elemental analysis: $C_{17}H_{20}O_3S$

Calcd.: C, 67.08; H, 6.62.

Found : C, 67.33; H, 6.68.

EXAMPLE 10

In DMF (10 ml) was dissolved 6-cyclohexyl-3,4-dihydro-1H-2-benzothiopyran-4-one-1-carboxylic acid (500 mg) followed by addition of diethyl phosphorocyanidate (85%, 365 mg). The mixture was stirred for 30 minutes under ice-cooling and, then, 3-aminopyridine (160 mg) and triethylamine (202 mg) were added thereto. The reaction mixture was further stirred for one hour under ice-cooling and poured into water and extracted with ethyl acetate. The ethyl acetate layer was washed with water, dried ($MgSO_4$) and the solvent was distilled off to give 6-cyclohexyl-N-(3-pyridyl)-3,4-dihydro-1H-2-benzothiopyran-4-one-1-carboxamide (490 mg, yield 79%). Recrystallization from ethyl acetate-hexane gave colorless plates.

mp. 194°-195° C.

Elemental analysis: $C_{21}H_{22}N_2O_2S$

Calcd.: C, 68.82; H, 6.05; N, 7.64.

Found ; C, 68.59; H, 5.90; N, 7.63.

EXAMPLES 11 THROUGH 55

In the same manner as Example 10, compounds in Table 10 were obtained.

TABLE 10

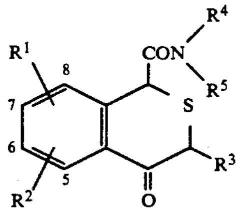

| Example No. | $R^1$, $R^2$ | $R^3$ | $R^4$, $R^5$ | Yield (%) | mp (°C.) | Recrystallization solvent |
|---|---|---|---|---|---|---|
| 11 | H, 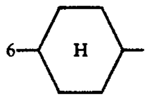 | H | H, 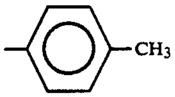 | 87 | 181-182 | Ethyl acetate |
| 12 | H, 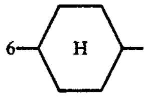 | H | H, 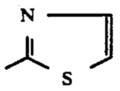 | 70 | 255-256 | Ethyl acetate |
| 13 | H, 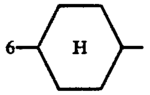 | H | 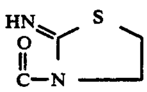 | 12 | 203-204 | Ethyl acetate |
| 14 | H, 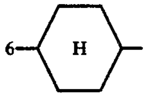 | H | H, 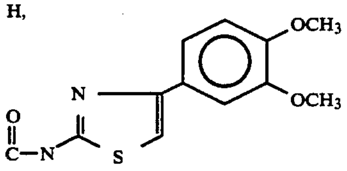 | 49 | 220-221 | Ethyl acetate |
| 15 | H, 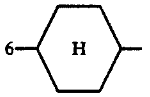 | H | H, 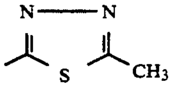 | 59 | 290-291 | Ethyl acetate |

TABLE 10-continued
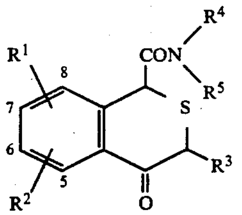
| Example No. | $R^1$, $R^2$ | $R^3$ | $R^4$, $R^5$ | Yield (%) | mp (°C.) | Recrystal-lization solvent |
|---|---|---|---|---|---|---|
| 16 | H, 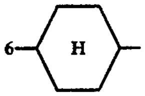 | H | H, 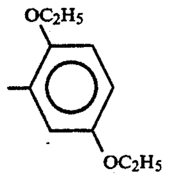 | 52 | 117-118 | Ethyl acetate-hexane |
| 17 | H, 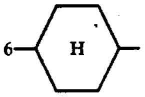 | H | H, 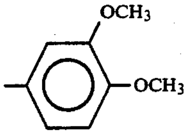 | 75 | 206-207 | Chloroform-methanol |
| 18 | H, 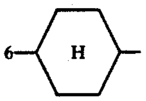 | H | 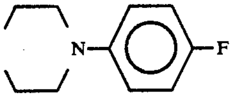 | 78 | 250-251 | Chloroform-methanol |
| 19 | H, 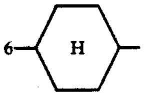 | H | H, 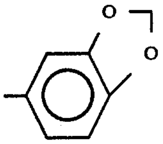 | 82 | 183-184 | Ethyl acetate-hexane |
| 20 | H, 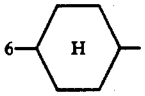 | H | H, 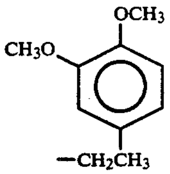 | 60 | 208-209 | Ethyl acetate |
| 21 | H, 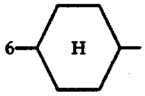 | H | H, 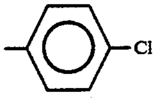 | 60 | 176-177 | Ethyl acetate-hexane |
| 22 | H, 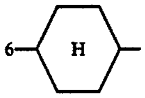 | H | H, 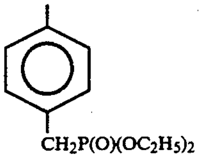 | 86 | 171-172 | Ethanol |

TABLE 10-continued
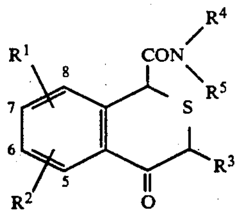
| Example No. | $R^1$, $R^2$ | $R^3$ | $R^4$, $R^5$ | Yield (%) | mp (°C.) | Recrystallization solvent |
|---|---|---|---|---|---|---|
| 23 | H, 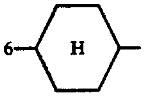 | $CH_3$ | H, 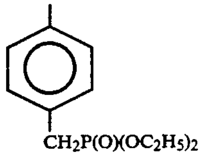 | 63 | Note 1) 164–165 | Methanol |
| 24 | H, 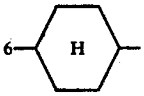 | H | H, 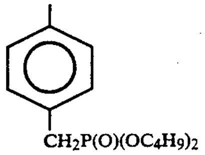 | 84 | 133–134 | Ethyl acetate-hexane |
| 25 | H, 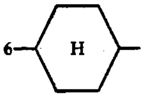 | H | H, 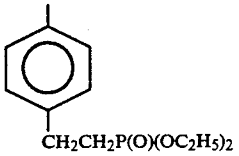 | 75 | 181–182 | Ethyl acetate-hexane |
| 26 | H, 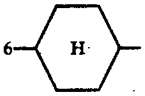 | H | H, 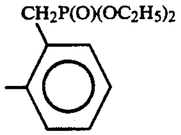 | 84 | 119–120 | Ethanol |
| 27 | 6,7-$(CH_2)_4$— | H | H, 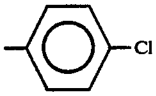 | 89 | 225–226 | Ethyl acetate-hexane |
| 28 | 6,7-$(CH_2)_4$— | H | H, 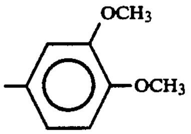 | 77 | 229–230 | Chloroform-methanol |
| 29 | 6,7-$(CH_2)_4$— | H | H, 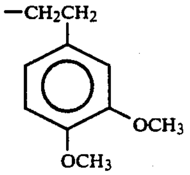 | 70 | 206–207 | Chloroform-methanol |

TABLE 10-continued
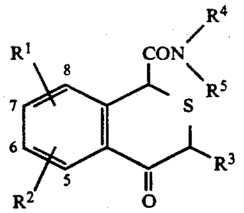
| Example No. | $R^1$, $R^2$ | $R^3$ | $R^4$, $R^5$ | Yield (%) | mp (°C.) | Recrystal-lization solvent |
|---|---|---|---|---|---|---|
| 30 | 6,7-$(CH_2)_4$— | H | 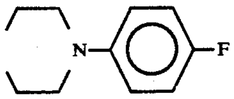 | 85 | 183–184 | Methanol |
| 31 | 6,7-$(CH_2)_4$— | H | H, 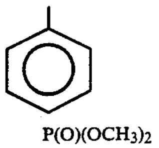 | 85 | 217–218 | Methanol |
| 32 | 6,7-$(CH_2)_4$— | H | H, 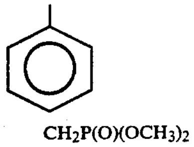 | 88 | 199–200 | Methanol |
| 33 | 6,7-$(CH_2)_4$— | H | H, 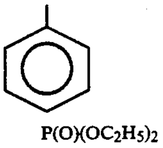 | 81 | 197–198 | Ethanol |
| 34 | 6,7-$(CH_2)_4$— | H | H, 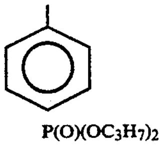 | 69 | 205–206 | Ethanol |
| 35 | 6,7-$(CH_2)_4$— | H | H, 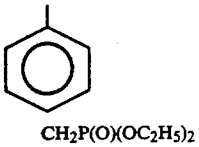 | 91 | 177–178 | Ethanol |
| 36 | 6,7-$(CH_2)_4$— | H | H, 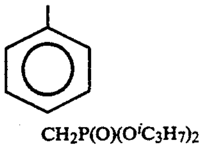 | 89 | 132–133 | Ethanol |

TABLE 10-continued
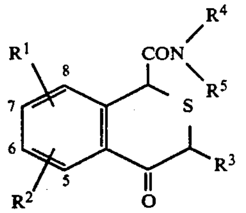
| Example No. | $R^1$, $R^2$ | $R^3$ | $R^4$, $R^5$ | Yield (%) | mp (°C.) | Recrystallization solvent |
|---|---|---|---|---|---|---|
| 37 | 6,7-$(CH_2)_4$— | H | H, 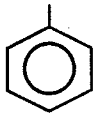 $CH_2P(O)(OC_4H_9)_2$ | 76 | 154-155 | Ethyl acetate-hexane |
| 38 | H, H | H | H, 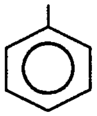 $P(O)(OC_2H_5)_2$ | 80 | 210-211 | Ethanol |
| 39 | H, H | H | H, 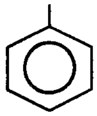 $CH_2P(O)(OC_2H_5)_2$ | 78 | 202-203 | Ethanol |
| 40 | H, H | H | H, 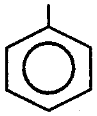 $P(O)(OC_3H_7)_2$ | 76 | 168-169 | Methanol |
| 41 | H, H | H | H, 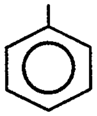 $CH_2P(O)(O^iC_3H_7)_2$ | 88 | 193-194 | Ethanol |
| 42 | H, 6-$C_6H_{13}$ | H | H, 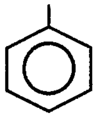 $CH_2P(O)(O^iC_3H_7)_2$ | 80 | 123-124 | Ethyl acetate-hexane |
| 43 | H, 6-$C_6H_{13}$ | H | H, 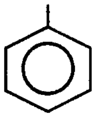 $P(O)(OC_2H_5)_2$ | 82 | 139-140 | Ethanol |

TABLE 10-continued
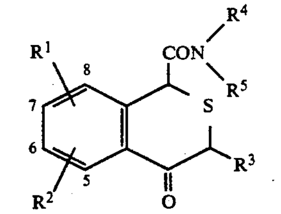
| Example No. | $R^1$, $R^2$ | $R^3$ | $R^4$, $R^5$ | Yield (%) | mp (°C.) | Recrystal-lization solvent |
|---|---|---|---|---|---|---|
| 44 | H, 6-$C_6H_{13}$ | H | H, 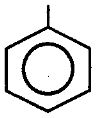 $CH_2P(O)(OC_2H_5)_2$ | 86 | 136–137 | Ethanol |
| 45 | H, 6-Cl | H | H, 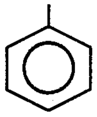 $P(O)(OCH_3)_2$ | 81 | 168–169 | Ethyl acetate |
| 46 | H, 6-Cl | H | H, 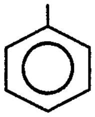 $P(O)(OC_2H_5)_2$ | 81 | 184–185 | Methanol |
| 47 | H, 6-Cl | H | H, 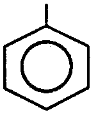 $P(O)(OC_3H_7)_2$ | 83 | 188–189 | Ethanol |
| 48 | H, 6-Cl | H | H, 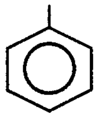 $CH_2P(O)(OC_2H_5)_2$ | 77 | 166–167 | Ethyl acetate-hexane |
| 49 | H, 6-Cl | H | H, 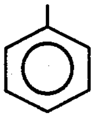 $CH_2P(O)(O^iC_3H_7)_2$ | 75 | 193–194 | Ethanol |
| 50 | 6,7-$O(CH_2)_2O$— | H | H, 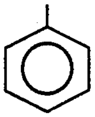 $P(O)(OC_3H_7)_2$ | 80 | 175–176 | Ethanol |

TABLE 10-continued

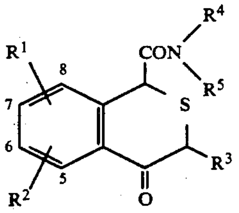

| Example No. | $R^1$, $R^2$ | $R^3$ | $R^4$, $R^5$ | Yield (%) | mp (°C.) | Recrystallization solvent |
|---|---|---|---|---|---|---|
| 51 | 6,7-$O(CH_2)_2O$— | H | H, 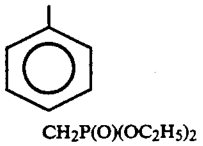 | 81 | 250–251 | Ethanol-chloroform |
| 52 | 6,7-$O(CH_2)_2O$— | H | H, 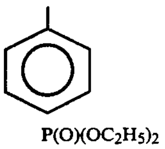 | 88 | 223–224 | Methanol-chloroform |
| 53 | 6,7-$(OCH_3)_2$ | H | 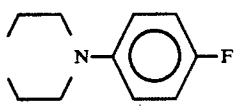 | 85 | 195–196 | Methanol |
| 54 | 6,7-$(OCH_3)_2$ | H | 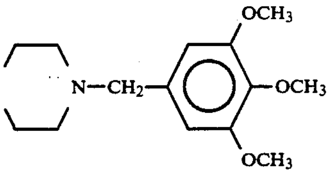 | 87 | Note 2) 222–223 | Methanol |
| 55 | H, 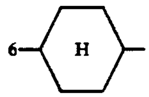 | H | $CH_3$, 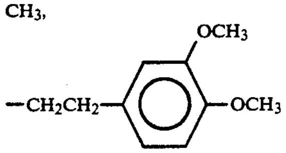 | 53 | 93–94 | Ether-hexane |

Note 1) 1,3-trans-Isomer
Note 2) Hydrochloride

EXAMPLE 56

A mixture of 7-cyclohexyl-1,2,4,5-tetrahydro-3-benzothiepin-5-one-2-carboxylic acid (1.0 g) and thionyl chloride (2 ml) was heated under reflux for 30 minutes and, then, concentrated. The residual oil was dissolved in dichloromethane (5 ml). This solution was added dropwise to a solution of 4-diethoxyphosphorylaniline (757 mg) in pyridine (10 ml) at room temperature. After stirring for 30 minutes at room temperature, the reaction mixture was concentrated. The residue was diluted with 1N-HCl (50 ml) and extracted with ethyl acetate. The ethyl acetate layer was washed with water, dried ($MgSO_4$) and the solvent was distilled off to give 7-cyclohexyl-N-(4-diethoxyphosphorylphenyl)-1,2,4,5-tetrahydro-3-benzothiepin-5-one-2-carboxamide (760 mg, yield 45%). Recrystallization from ethanol gave colorless prisms.

m.p. 222°-223° C.

Elemental analysis: $C_{27}H_{34}NO_5PS$

Calcd.: C, 62.90; H, 6.65; N, 2.72.

Found: C, 62.79; H, 6.55; N, 2.71.

EXAMPLES 57 AND 58

In the same manner as Example 56, the compounds in Table 11 were obtained.

TABLE 11

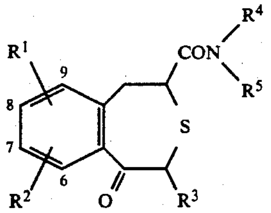

| Example No. | R¹, R² | R³ | R⁴, R⁵ | Yield (%) | mp (°C.) | Recrystallization solvent |
|---|---|---|---|---|---|---|
| 57 | H, 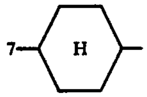 | H | H, 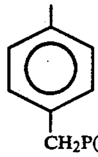 $CH_2P(O)(OC_2H_5)_2$ | 77 | 235-236 | Methanol-chloroform |
| 58 | H, 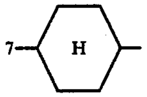 | H | H, 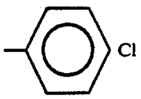 | 60 | 227-228 | Methanol-chloroform |

EXAMPLE 59

Sodium borohydride (102 mg) was added to a solution of 7-cyclohexyl-N-(3,4-methylenedioxyphenyl)-3,4-dihydro-1H-2-benzothiopyran-4-one-1-carboxamide (1.1 g) in ethanol (20 ml) and the mixture was stirred at room temperature for 2 hours. After addition of acetic acid (1 ml), the reaction mixture was poured into water and extracted with ethyl acetate. The ethyl acetate layer was successively washed with water, saturated aqueous solution of $NaHCO_3$ and water, dried ($MgSO_4$) and the solvent was distilled off to give 7-cyclohexyl-N-(3,4-methylenedioxyphenyl)-c-4-hydroxy-3,4-dihydro-1H-2-benzothiopyran-r-1-carboxamide (0.97 g, yield 88%). Recrystallization from ethyl acetate gave colorless prisms.

mp. 208°-209° C.

Elemental analysis: $C_{23}H_{25}NO_4S$

Calcd.: C, 67.13; H, 6.12; N, 3.40.

Found: C, 66.91; H, 6.19; N, 3.15.

EXAMPLES 60 THROUGH 62

In the same manner as Example 59, the compounds in Table 12 were obtained.

TABLE 12

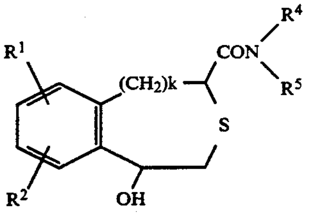

| Example No. | R¹, R² | R⁴, R⁵ | K | Yield (%) | mp (°C.) |
|---|---|---|---|---|---|
| 60 | H, 6- 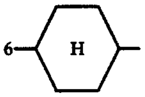 | H, 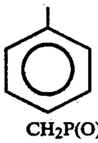 $CH_2P(O)(OC_2H_5)_2$ | 0 | 82 | Note 1) 88-89 |
| 61 | 6.7-$(CH_2)_4$— | H, 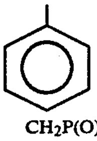 $CH_2P(O)(OC_2H_5)_2$ | 0 | 85 | Note 2) 70-71 |

TABLE 12-continued

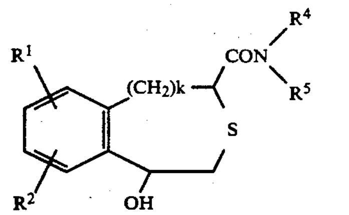

| Example No. | $R^1$, $R^2$ | $R^4$, $R^5$ | K | Yield (%) | mp (°C.) |
|---|---|---|---|---|---|
| 62 | H, 7— 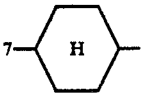 | H, 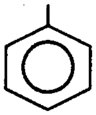 $CH_2P(O)(OC_2H_5)_2$ | 1 | 83 | Note 3) 120–122 |

Note 1) Powder, a 2:1 mixture of 1,4-cis- and trans-isomers
Note 2) Powder, a 3:1 mixture of 1,4-cis- and trans-isomers
Note 3) Recrystallization ethyl acetate, a 2:1 mixture of 2,5-cis- and trans-isomers

EXAMPLE 63

A solution of m-chloroperbenzoic acid (70%, 662 mg) in chloroform (5 ml) was added to a solution of 7-cyclohexyl-N-(3,4-methylenedioxyphenyl)-3,4-dihydro-1H-2-benzothiopyran-4-one-1-carboxamide (1.1 g) in chloroform (15 ml) under ice-cooling and the mixture was stirred for 1 hour at the same teperature. The reaction mixture was successively washed with water, saturated aqueous solution of $NaHCO_3$ and water, dried ($MgSO_4$) and the solvent was distilled off. The residue was subjected to silica gel chromatography with ethyl acetate-hexane (2:3, v/v). Removal of the solvent from the first eluate gave 7-cyclohexyl-N-(3,4-methylenedioxyphenyl)-3,4-dihydro-1H-2-benzothiopyran-4-one-1-carboxamide-2,2-dioxide (0.28 g, yield 23%). Recrystallization from ethyl acetate-hexane gave colorless needles.

mp. 224°–225° C.

Elemental analysis: $C_{23}H_{23}NO_6S$

Calcd.: C, 62.57; H, 5.25; N, 3.17.

Found: C, 62.41; H, 5.23; N, 3.21.

Solvent removal from the following eluate gave 7-cyclohexyl-N-(3,4-methylenedioxyphenyl)-3,4-dihydro-1H-2-benzothiopyran-4-one-1-carboxamide-2-oxide (0.58 g, yield 53%) (a mixture of 1,2-cis and -trans, 6:4). Recrystallization from ethanol gave colorless prisms.

mp. 208°–209° C.

Elemental analysis: $C_{23}H_{23}NO_5S$

Calcd.: C, 64.92; H, 5.45; N, 3.29.

Found: C, 64.57; H, 5.28; N, 3.45.

EXAMPLES 64 THROUGH 67

In the same manner as Example 63, the compounds in Table 13 were obtained.

TABLE 13

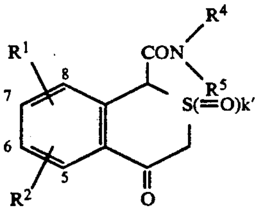

| Example No. | $R^1$, $R^2$ | $R^4$, $R^5$ | k' | Yield (%) | mp (°C.) | Recrystallization solvent |
|---|---|---|---|---|---|---|
| 64 | H, 6— 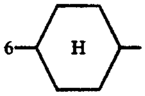 | H, 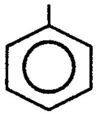 $CH_2P(O)(OC_2H_5)_2$ | 1 | 73 | Note 1) 140–142 | Ethyl acetate-hexane |
| 65 | H, 6— 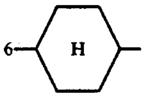 | H, 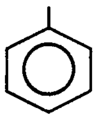 $CH_2P(O)(OC_2H_5)_2$ | 2 | 16 | 179–180 | Ethyl |

TABLE 13-continued

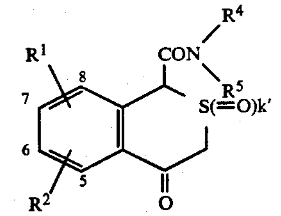

| Example No. | $R^1, R^2$ | $R^4, R^5$ | k' | Yield (%) | mp (°C.) | Recrystallization solvent |
|---|---|---|---|---|---|---|
| 66 | 6,7-$(CH_2)_4$— | 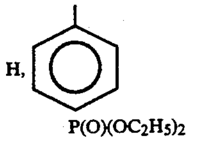 | 1 | 11 | Note 2) 145-147 | Ethyl acetate-hexane |
| 67 | 6,7-$(CH_2)_4$— | 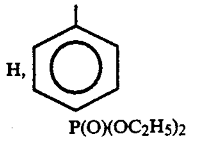 | 2 | 11 | Note 3) 128-130 | Ethyl acetate-hexane |

Note 1) 1:1 (ca.) mixture of cis- and trans-isomers
Note 2) Powder, a 1:1 (ca.) mixture of cis- and trans-isomers
Note 3) Powder

EXAMPLE 68

To a solution of 7-cyclohexyl-N-(4-diethoxyphosphorylmethylphenyl)-1,2,3,4-, 5-tetrahydro-3-benzothiepin-5-one-2-carboxamide (0.53 g) in chloroform (10 ml) was added dropwise a solution of m-chloroperbenzoic acid (80%, 0.6478) in chloroform (10 ml), and the mixture was allowed to stand at room temperature overnight. The reaction mixture was then successively washed with aqueous potassium carbonate solution and water, dried ($MgSO_4$). The solvent was then distilled off to give 7-cyclohexyl-N-(4-diethoxyphosphorylmethylphenyl)-1,2,4,5-tetrahydro-3-benzothiepin-5-one-2-carboxamide-3,3-dioxide (0.49 g, 87%). Recrystallization from chloroform-ethanol gave colorless plates melting at 237°-238° C.

Elemental analysis, $C_{28}H_{38}NO_7PS$

Calcd.: C, 59.88; H, 6.46; N, 2.49.

Found: C, 59.77; H, 6.53; N, 2.66.

In substantially the same manner as Example 68, the compounds shown in Table 14 were obtained.

TABLE 14

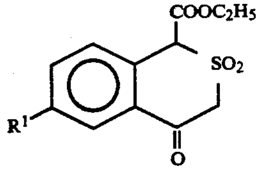

| Example No. | $R^1$ | Yield (%) | M.p. (°C.) | Recrystallization solvent |
|---|---|---|---|---|
| 69 | 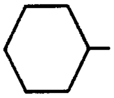 | 91 | 90-91 | Ethyl acetate-hexane |

TABLE 14-continued

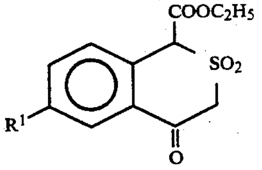

| Example No. | $R^1$ | Yield (%) | M.p. (°C.) | Recrystallization solvent |
|---|---|---|---|---|
| 70 | $CH_3$ | 38 | 84-85 | Ethyl acetate-hexane |

EXAMPLE 71

A mixture of ethyl 6-methyl-3,4-dihydro-1H-2-benzothiopyran-4-one-1-carboxylate-2,2-dioxide (0.565 g), 2N-KOH (10 ml) and methanol (10 ml) was stirred at room temperature for 30 minutes, after which it was acidified with 2N-HCl and extracted with ethyl acetate. The ethyl acetate layer was washed with water, dried ($MgSO_4$) and the solvent was distilled off. To the residue was added thionyl chloride (2 ml) and the mixture was refluxed for 30 minutes and, then, concentrated under reduced pressure. The oily residue was dissolved in dichloromethane (5 ml) and the solution was added dropwise to a solution of diethyl 4-aminobenzylphosphonate (0.487 mg) in pyridine (10 ml) at room temperature. The mixture was stirred at room temperature for 30 minutes, after which it was poured into water and extracted with ethyl acetate. The ethyl acetate layer was successively washed with 2N-HCl and water, dried ($MgSO_4$) and the solvent was distilled off to give N-(4-diethoxyphosphorylmethylphenyl)-6-methyl-3,4-dihydro-1H-2-benzothiopyran-4-one-1-carboxamide-2,2-dioxide (0.32 g, 33%). Recrystallization from ethanol gave colorless needles melting at 212°-213° C.

Elemental analysis, $C_{22}H_{26}NO_7PS$
Calcd.: C, 55.11; H, 5.47; N, 2.92.
Found C, 55.37; H, 5.62; N, 2.89.

EXAMPLE 72

In substantially the same manner as Example 71, N-(diethoxyphosphorylphenyl)-6-methyl-3,4-dihydro-1H-2-benzothiopyran-4-one-1-carboxamide-2,2-dioxide was synthesized. Yield 55%. Recrystallization from ethyl acetate—hexane gave colorless prisms melting at 129°-130° C.

Elemental analysis, $C_{21}H_{24}NO_7PS$
Calcd.: C, 54.19; H, 5.20; N, 3.01.
Found: C, 54.14; H, 5.39; N, 2.92.

EXAMPLE 73

In ether (300 ml) was dissolved ethoxycarbonyl(3,4-dimethylphenyl)methylthioacetic acid (66 g) followed by addition of thionyl chloride (41.7 g) and, then, pyridine (0.1 ml). The mixture was stirred at room temperature for 1 hour and, then, refluxed for 30 minutes, after which it was concentrated under reduced pressure. The oily residue was dissolved in dichloromethane (100 ml) and the solution was added dropwise to an ice-cooled suspension of aluminum chloride (62.4 g) in dichloromethane (300 ml) over a period of 1 hour. The reaction mixture was further stirred with ice-cooling for 1 hour, after which it was poured into ice-water (1 l) and the organic layer was separated. The organic layer was washed with water, dried ($MgSO_4$) and the solvent was distilled off to give ethyl 6,7-dimethyl-3,4-dihydro-1H-2-benzothiopyran-4-one-1carboxylate (49.5 g, 80%). Recrystallization from hexane gave coloreless plates melting at 68°-69° C.

Elemental analysis, $C_{14}H_{16}O_3S$
Calcd.: C, 63.61; H, 6.10.
Found: C, 63.68; H, 6.15.

EXAMPLES 74 THROUGH 88

In substantially the same manner as Example 73, the compounds shown in Table 15 were obtained.

TABLE 15

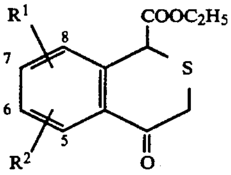

| Example No. | $R^1$, $R^2$ | Yield (%) | mp (°C.) | Recrystallization solvent | NMR (δ ppm, $CDCl_3$) |
|---|---|---|---|---|---|
| 74 | H, 6-$CH_3$ | 73 | Oil | | 1.29(3H, t, J=7), 2.38(3H, s), 3.26(1H, d, J=16), 4.22(2H, q, J=7), 4.27(1H, d, J=16), 4.40(1H, s), 7.12(2H, d, J=8), 7.31(1H, dd, J=8,2), 7.95(1H, d, J=2). |
| 75 | H, 6-$(CH_3)_2CH$— | 70 | Oil | | 1.26(6H, d, J=7), 1.31(3H, t, J=7), 2.9 5(1H, m), 3.27(1H, dd, J=16,1), 4.24 (2H, q, J=7), 4.27(1H, d, J=16), 4.42 (1H, s), 7.11(2H, d, J=8), 7.31(1H, dd, J=8,2), 8.00(1H, d, J=2). |
| 76 | H, 6-$(CH_3)_3C$— | 80 | Oil | | 1.30(3H, t, J=7), 1.31(9H, s), 3.22(1H, d, J=16), 4.20(2H, q, J=7), 4.28(1H, d, J=16), 4.40(1H, s), 7.15(1H, d, J=8), 7.52(1H, dd, J=8,2). |
| 77 | H, 6-$C_2H_5C(CH_3)_2$— | 84 | Oil | | 0.67(3H, t, J=7), 1.27(3H, t, J=7), 1.2 8(6H, s), 1.65(2H, q, J=7), 3.23(1H, d, J=16), 4.22(2H, q, J=7), 4.28(1H, d, J=16), 4.40(1H, s), 7.17(1H, d, J=8), 7.4 6(1H, dd, J=8,2), 8.10(1H, d, J=2). |
| 78 | H, 6-$(CH_3)_3CCH_2$— | 63 | Oil | | 0.91(9H, s), 1.30(3H, t, J=7), 2.54(2 H, s), 3.27(1H, dd, J=16,1), 4.24(2H, q, J=7), 4.27(1H, d, J=16), 4.43(1H, s), 7.13(1H, d, J=8), 7.24(1H, dd, J=8,2), 7.89(1H, d, J=2). |
| 79 | H, 6- 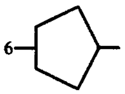 | 78 | Oil | | 1.30(3H, t, J=7), 1.3-2.2(8H, m), 2.65 (1H, m), 3.20(1H, d, J=16), 4.21(2H, q, J=7), 4.26(1H, d, J=16), 4.39(1H, s), 7.15(1H, d, J=8), 7.31(1H, dd, J=8,2), 7.93(1H, d, J=2). |
| 80 | H, 6- 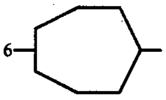 | 87 | Oil | | 1.28(3H, t, J=7), 1.3-2.1(12H, m), 2.70(1H, m), 3.22(1H, d, J=16), 4.20(2H, q, J=7), 4.26(1H, d, J=16), 4.39(1H, s), 7.12(1H, d, J=8), 7.31(1H, dd, J=8,2), 7.93(1H, d, J=2). |
| 81 | H, 6- 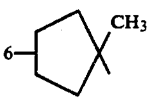 | 81 | Oil | | 1.21(3H, s), 1.26(3H, t, J=7), 1.5-2.1 (8H, m), 3.25(1H, d, J=16), 4.20(2H, q, J=7), 4.26(1H, d, J=16), 4.38(1H, s), 7.12(1H, d, J=8), 7.43(1H, dd, J=8,2), 8.06(1H, d, J=2). |

TABLE 15-continued

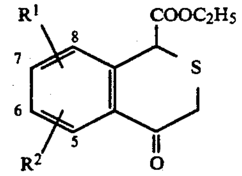

| Example No. | $R^1$, $R^2$ | Yield (%) | mp (°C.) | Recrystallization solvent | NMR (δ ppm, $CDCl_3$) |
|---|---|---|---|---|---|
| 82 | H, 6— 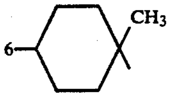 | 84 | Oil | | 1.16(3H, s), 1.28(3H, t, J=7), 1.3-2.1 (10H, m), 3.23(1H, d, J=16), 4.22(2H, q, J=7), 4.28(1H, d, J=16), 4.40(1H, s), 7.12(1H, d, J=8), 7.42(1H, dd, J=8,2), 8.07(1H, d, J=8). |
| 83 | 5-$CH_3$, 8-$CH_3$ | 73 | 102-103 | Ethyl acetate-hexane | |
| 84 | 6-$CH_3$, 8-$CH_3$ | 69 | 79-80 | Ethyl acetate-hexane | |
| 85 | 6-$C_2H_5$, 7-$C_2H_5$ | 80 | Oil | | 1.20(3H, t, J=7), 1.22(3H, t, J=7), 1.31(3H, t, J=7), 2.67(4H, q, J=7), 3.22 (1H, d, J=16), 4.24(2H, q, J=7), 4.28 (1H, d, J=16), 4.38(1H, s), 7.0(1H, s), 7.93(1H, s). |
| 86 | 6-$(CH_3)_2CH$—, 7-$(CH_3)_2CH$— | 56 | 113-114 | Hexane | |
| 87 | 6,7-$(CH_2)_3$— | 83 | Oil | | 1.28(3H, t, J=7), 2.0-2.3(2H, m), 2.92 (4H, t, J=7), 3.22(1H, d, J=16), 4.21 (1H, d, J=16), 4.22(2H, q, J=7), 4.38 (1H, s), 7.07(1H, s), 7.96(1H, s). |
| 88 | 6,7-$(CH_2)_5$— | 81 | 78-79 | Hexane | |

EXAMPLE 89

In ether (300 ml) was dissolved 2-[ethoxycarbonyl(3,4-dimethylphenyl)methylthio]propionic acid (40.5 g), followed by addition of thionyl chloride (24.4 g) and, then, pyridine (0.1 ml). The mixture was stirred at room temperature for 1 hour and refluxed for 30 minutes. The solvent was distilled off under reduced pressure and the oily residue was dissolved in dichloromethane (80 ml). This solution was added dropwise to an ice-cooled suspension of aluminum chloride (38.4 g) in dichloromethane (300 ml) over a period of 1 hour. The reaction mixture was further stirred for 1.5 hours with ice-cooling and, then, poured into ice-water (1 l). The organic layer was separated, washed with water, dried ($MgSO_4$) and the solvent was distilled off. The oily residue was dissolved in ethanolic sodium ethoxide (prepared from 0.315 g of sodium and 200 ml of ethanol) and the solution was refluxed for 15 minutes. The reaction mixture was then poured into water, acidified with 1N-HCl (100 ml) and extracted with ether. The ether layer was washed with water, dried ($MgSO_4$) and the solvent was distilled off. Finally, the residue was chromatographed on a silica gel with ether-hexane (1:3) to give ethyl 6,7-dimethyl-t-3-methyl-3,4-dihydro-1H-2-benzothiopyran-4-one-r-1-carboxylate (23.5 g, 62%). Recrystallization from hexane gave colorless prisms melting at 83°-84° C.

Elemental analysis, $C_{15}H_{18}O_3S$

Calcd.: C, 64.72; H, 6.52.

Found: C, 64.90; H, 6.55.

EXAMPLES 90 THROUGH 94

In substantially the same manner, the compounds shown in Table 16 were obtained.

TABLE 16

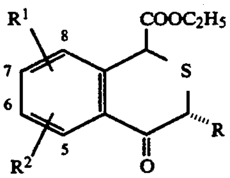

| Example No. | $R^1$, $R^2$ | R | Yield (%) | mp (°C.) | Recrystallization solvent | NMR(δ ppm, $CDCl_3$) |
|---|---|---|---|---|---|---|
| 90 | 6-$CH_3$, 7-$CH_3$ | $C_2H_5$ | 51 | Oil | | 1.05(3H, t, J=7), 1.31(3H, t, J=7), 1.6-1.8(2H, m), 2.28(6H, s), 4.22 (1H, t, J=7), 4.24(2H, q, J=7), 4.43 (1H, s), 6.96(1H, s), 7.81(1H, s). |
| 91 | 6-$CH_3$, 7-$CH_3$ | $C_3H_7$ | 53 | Oil | | 0.97(3H, t, J=7), 1.31(3H, t, J=7), 1.4-1.8(4H, m), 2.28(6H, s), 4.24 (2H, q, J=7), 4.31(1H, t, J=7), 4.42 |

TABLE 16-continued

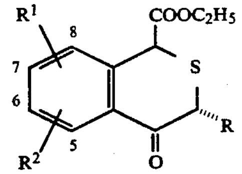

| Example No. | $R^1$, $R^2$ | R | Yield (%) | mp (°C.) | Recrystallization solvent | NMR(δ ppm, $CDCl_3$) |
|---|---|---|---|---|---|---|
| | | | | | | (1H, s), 6.97(1H, s), 7.81(1H, s). |
| 92 | 6-$CH_3$, 7-$CH_3$ | 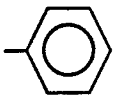 | 30 | 116–117 | Ethyl acetate-hexane | |
| 93 | 6,7-$(CH_2)_3$— | $CH_3$ | 48 | 77–78 | Hexane | |
| 94 | 6,7-$(CH_2)_4$— | $CH_3$ | 43 | 86–87 | Hexane | |

EXAMPLE 95

A mixture of ethyl 6,7-dimethyl-t-3-methyl-3,4-dihydro-1H-2-benzothiopyran-4-one-r-1-carboxylate (21 g), 2N-KOH (100 ml) and methanol (100 ml) was stirred at 50½° C. for 30 minutes, at the end of which time it was acidified with 1N-HCl and extracted with ethyl acetate. The ethyl acetate layer was washed with water, dried ($MgSO_4$) and the solvent was distilled off under reduced pressure. The procedure yielded 6,7-dimethyl-t-3-methyl-3,4-dihydro-1H-2-benzothiopyran-4-one-r-1-carboxylic acid (16.5 g, 87%). Recrystallization from ethyl acetate gave colorless prisms melting at 203°-204° C.

Elemental analysis, $C_{13}H_{14}O_3S$

Calcd.: C, 62.38; H, 5.64.

Found: C, 62.67; H, 5.67.

EXAMPLES 96 THROUGH 116

In substantially the same manner as Example 95, the compounds shown in Table 17 were obtained.

TABLE 17

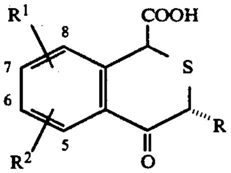

| Example No. | $R^1$, $R^2$ | R | Yield (%) | mp (°C.) | Recrystallization solvent |
|---|---|---|---|---|---|
| 96 | H, 6-$CH_3$ | H | 79 | 185–168 | Ethyl acetate-hexane |
| 97 | H, 6-$(CH_3)_2CH$— | H | 76 | 110–111 | Ethyl acetate-hexane |
| 98 | H, $(CH_3)_3C$— | H | 78 | 190–191 | Ethyl acetate-hexane |
| 99 | H, 6-$C_2H_5C(CH_3)_2$— | H | 73 | 158–159 | Ether-hexane |
| 100 | H, 6-$(CH_3)_3C.CH_2$— | H | 78 | 146–147 | Ethyl acetate-hexane |
| 101 | H,6- 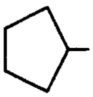 | H | 88 | 124–125 | Ethyl acetate-hexane |
| 102 | H,6- 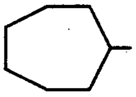 | H | 68 | 166–167 | Ethyl acetate-hexane |
| 103 | H,6- 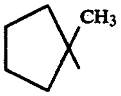 | H | 63 | 155–156 | Ethyl acetate-hexane |
| 104 | H,6- 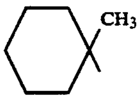 | H | 49 | 165–166 | Ethyl acetate-hexane |
| 105 | 5-$CH_3$, 8-$CH_3$ | H | 97 | 194–195 | Ethyl acetate |
| 106 | 6-$CH_3$, 8-$CH_3$ | H | 94 | 168–169 | Ethyl acetate-hexane |

TABLE 17-continued

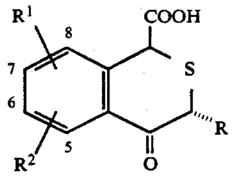

| Example No. | $R^1$, $R^2$ | R | Yield (%) | mp (°C.) | Recrystallization solvent |
|---|---|---|---|---|---|
| 107 | 6-$CH_3$, 7-$CH_3$ | H | 78 | 183–184 | Ethyl acetate |
| 108 | 6-$CH_3$, 7-$CH_3$ | $C_2H_5$ | 70 | 157–158 | Ethyl acetate-hexane |
| 109 | 6-$CH_3$, 7-$CH_3$ | $C_3H_7$ | 76 | 167–168 | Ethyl acetate-hexane |
| 110 | 6-$CH_3$, 7-$CH_3$ | 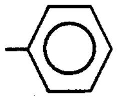 | 30 | 179–180 | Ethyl acetate |
| 111 | 6-$C_2H_5$, 7-$C_2H_5$ | H | 75 | 189–190 | Ethyl acetate |
| 112 | 6-$(CH_3)_2CH$—, 7-$(CH_3)_2CH$— | H | 97 | 144–145 | Ethyl acetate-hexane |
| 113 | 6,7-$(CH_2)_3$— | H | 75 | 177–178 | Ethyl acetate |
| 114 | 6,7-$(CH_2)_3$— | $CH_3$ | 71 | 192–193 | Ethyl acetate |
| 115 | 6,7-$(CH_2)_4$— | $CH_3$ | 78 | 185–186 | Ethyl acetate-hexane |
| 116 | 6,7-$(CH_2)_5$— | H | 75 | 204–205 | Ethyl acetate |

REFERENCE EXAMPLE 117 THROUGH 199

In substantially the same manner as Reference Example 10, the compounds shown in Table 18 were obtained.

TABLE 18
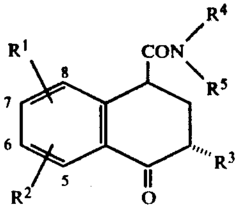
| Example No. | $R^1$, $R^2$ | $R^3$ | $R^4$, $R^5$ | Yield (%) | mp (°C.) | Recrystallization solvent |
|---|---|---|---|---|---|---|
| 117 | H, H | H | H, 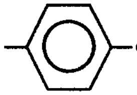 $CH_2P(O)(OC_4H_9)_2$ | 86 | 193–194 | Ethyl acetate-hexane |
| 118 | H, 6-Cl | H | H, 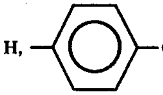 $CH_2P(O)(OCH_3)_2$ | 94 | 199–200 | Methanol |
| 119 | H, 6-$C_6H_{13}$ | H | H, 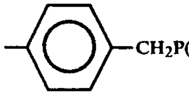 $CH_2P(O)(OC_4H_9)_2$ | 83 | 87–88 | Ether-hexane |
| 120 | 6,7-$OCH_2CH_2O$— | H | H, 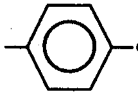 $CH_2P(O)(OiC_3H_7)_2$ | 91 | 253–254 | Ethanol chloroform |
| 121 | 6,7-$OCH_2CH_2O$— | H | H, 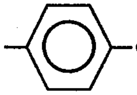 $CH_2P(O)(OC_4H_9)_2$ | 86 | 182–183 | Ethanol |
| 122 | H, 6— 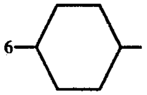 | H | H, —$CH_2$— 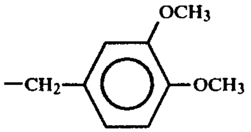 | 59 | 206–207 | Ethyl acetate |

TABLE 18-continued
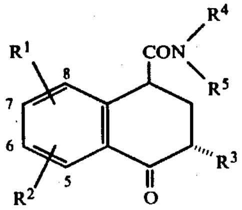
| Example No. | $R^1$, $R^2$ | $R^3$ | $R^4$, $R^5$ | Yield (%) | mp (°C.) | Recrystallization solvent |
|---|---|---|---|---|---|---|
| 123 | H, 6 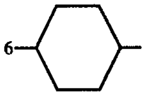 | H | H, 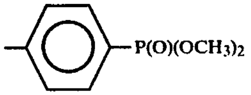 | 74 | 210–211 | Methanol |
| 124 | H, 6 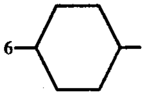 | H | H, 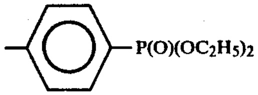 | 77 | 195–196 | Ethanol |
| 125 | H, 6 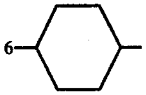 | H | H, 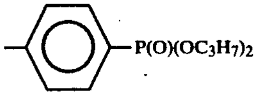 | 71 | 174–175 | Ethanol |
| 126 | H, 6 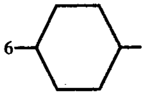 | H | H, 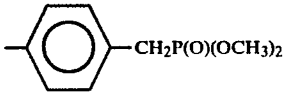 | 64 | 219–220 | Methanol |
| 127 | H, 6 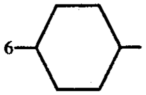 | H | H, 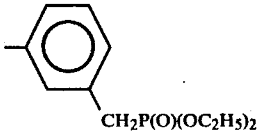 | 30 | Note 1) Oil | |
| 128 | H, 6 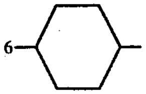 | H | H, 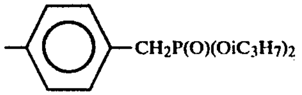 | 80 | 179–180 | Ethanol |

TABLE 18-continued
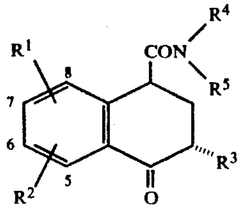
| Example No. | $R^1$, $R^2$ | $R^3$ | $R^4$, $R^5$ | Yield (%) | mp (°C.) | Recrystallization solvent |
|---|---|---|---|---|---|---|
| 129 | H, 6- 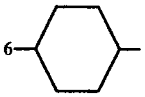 | H | H, $-CH_2CH_2P(O)(OC_2H_5)_2$ | 51 | Note 2) Oil | |
| 130 | H, 6- 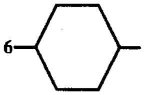 | H | H, $-CH_2CH_2CH_2P(O)(OC_2H_5)_2$ | 49 | 114–115 | Ethyl acetate-hexane |
| 131 | H, 6- 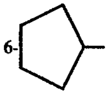 | H | H, 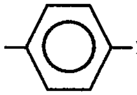 $P(O)(OC_2H_5)_2$ | 79 | 185–186 | Ethanol |
| 132 | H, 6- 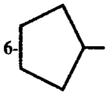 | H | H, 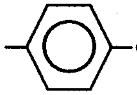 $CH_2P(O)(OC_2H_5)_2$ | 91 | 154–155 | Ethanol |
| 133 | H, 6- 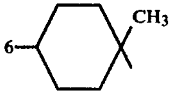 | H | H, 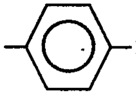 $P(O)(OC_2H_5)_2$ | 65 | 174–175 | Ethanol |
| 134 | H, 6- 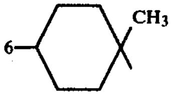 | H | H, 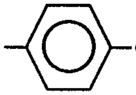 $CH_2P(O)(OC_2H_5)_2$ | 94 | 129–130 | Ether-hexane |
| 135 | H, 6- 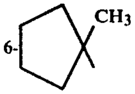 | H | H, 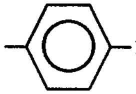 $P(O)(OC_2H_5)_2$ | 87 | 189–190 | Ethyl acetate |

TABLE 18-continued
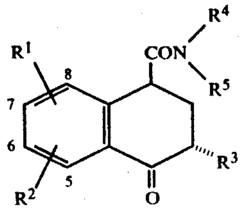
| Example No. | $R^1$, $R^2$ | $R^3$ | $R^4$, $R^5$ | Yield (%) | mp (°C.) | Recrystallization solvent |
|---|---|---|---|---|---|---|
| 136 | H, 6- 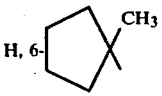 | H | H, 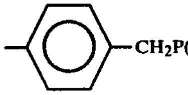 $-CH_2P(O)(OC_2H_5)_2$ | 92 | 144–145 | Ethyl acetate-hexane |
| 137 | H, 6- 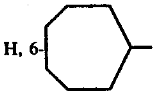 | H | H, 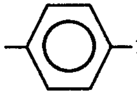 $-P(O)(OC_2H_5)_2$ | 93 | 186–187 | Ethanol |
| 138 | H, 6- 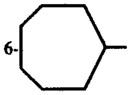 | H | H, 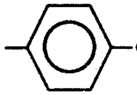 $-CH_2P(O)(OC_2H_5)_2$ | 83 | 181–182 | Ethanol |
| 139 | H, 6-$CH_3$ | H | H, 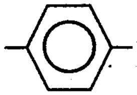 $-P(O)(OC_2H_5)_2$ | 91 | 167–168 | Ethyl acetate-hexane |
| 140 | H, 6-$CH_3$ | H | H, 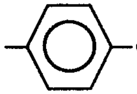 $-CH_2P(O)(OC_2H_5)_2$ | 89 | 169–170 | Ethanol |
| 141 | H, 6-$(CH_3)_2CH-$ | H | H, 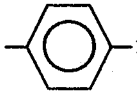 $-P(O)(OC_2H_5)_2$ | 88 | 209–210 | Ethyl acetate |

TABLE 18-continued
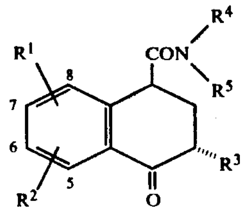
| Example No. | $R^1$, $R^2$ | $R^3$ | $R^4$, $R^5$ | Yield (%) | mp (°C.) | Recrystallization solvent |
|---|---|---|---|---|---|---|
| 142 | H, 6-$(CH_3)_2CH$— | H | H, 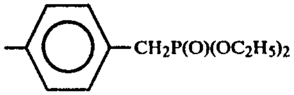 | 91 | 154–155 | Ethanol |
| 143 | H, 6-$(CH_3)_3C$— | H | H, 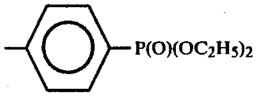 | 88 | 218–219 | Ethyl acetate |
| 144 | H, 6-$(CH_3)_3C$— | H | H, 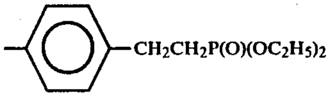 | 71 | 133–134 | Ethyl acetate-hexane |
| 145 | H, 6-$C_2H_5C(CH_3)_2$— | H | H, 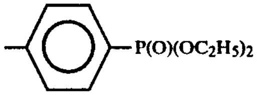 | 91 | 212–213 | Ethanol |
| 146 | H, 6-$C_2H_5C(CH_3)_2$— | H | H, 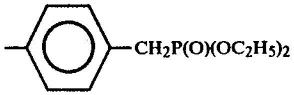 | 91 | 132–133 | Ethyl acetate-hexane |
| 147 | H, 6-$(CH_3)_3CCH_2$— | H | H, 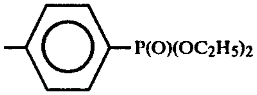 | 76 | 191–192 | Ethyl acetate-hexane |
| 148 | H, 6-$(CH_3)_3CCH_2$— | H | H, 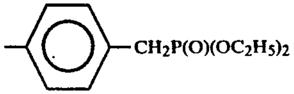 | 83 | 172–173 | Ethanol |

TABLE 18-continued
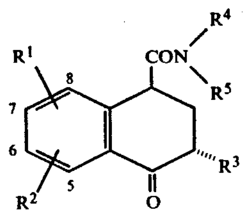
| Example No. | $R^1$, $R^2$ | $R^3$ | $R^4$, $R^5$ | Yield (%) | mp (°C.) | Recrystallization solvent |
|---|---|---|---|---|---|---|
| 149 | 5-$CH_3$, 8-$CH_3$ | H | 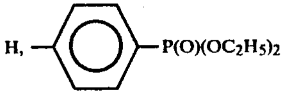 | 41 | 282-283 | Ethanol chloroform |
| 150 | 5-$CH_3$, 8-$CH_3$ | H | 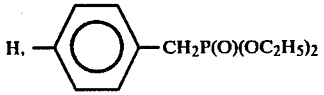 | 56 | 221-222 | Ethanol |
| 151 | 6-$CH_3$, 8-$CH_3$ | H | 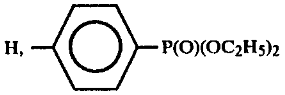 | 63 | 230-231 | Ethanol |
| 152 | 6-$CH_3$, 8-$CH_3$ | H | 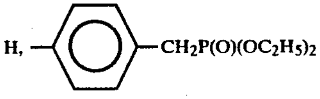 | 88 | 191-192 | Ethanol |
| 153 | 6-$CH_3$, 8-$CH_3$ | H | 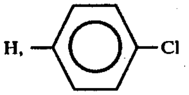 | 72 | 209-210 | Ethyl acetate-hexane |
| 154 | 6-$CH_3$, 7-$CH_3$ | H | 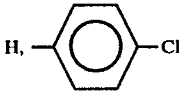 | 82 | 202-203 | Ethyl acetate-hexane |

TABLE 18-continued
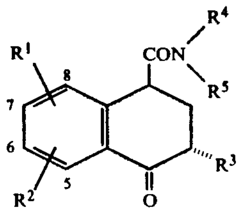
| Example No. | $R^1$, $R^2$ | $R^3$ | $R^4$, $R^5$ | Yield (%) | mp (°C.) | Recrystallization solvent |
|---|---|---|---|---|---|---|
| 155 | 6-$CH_3$, 7-$CH_3$ | H | 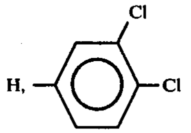 | 79 | 209-210 | Ethyl acetate-hexane |
| 156 | 6-$CH_3$, 7-$CH_3$ | H | 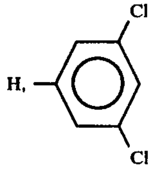 | 84 | 234-235 | Ethyl acetate |
| 157 | 6-$CH_3$, 7-$CH_3$ | H | 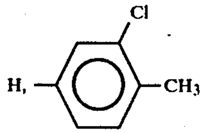 | 83 | 199-200 | Ethyl acetate |
| 158 | 6-$CH_3$, 7-$CH_3$ | H | 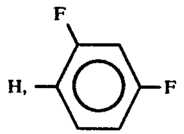 | 88 | 189-200 | Ethyl acetate-hexane |
| 159 | 6-$CH_3$, 7-$CH_3$ | H | 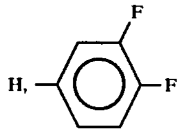 | 82 | 210-211 | Ethyl acetate-hexane |

TABLE 18-continued
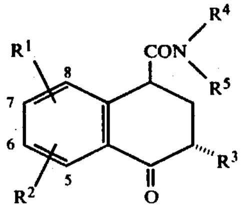
| Example No. | $R^1$, $R^2$ | $R^3$ | $R^4$, $R^5$ | Yield (%) | mp (°C.) | Recrystallization solvent |
|---|---|---|---|---|---|---|
| 160 | 6-$CH_3$, 7-$CH_3$ | H | H, 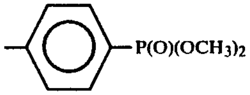 | 64 | 182–183 | Ethyl acetate-hexane |
| 161 | 6-$CH_3$, 7-$CH_3$ | H | H, 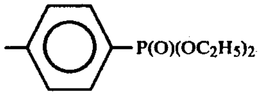 | 85 | 219–220 | Ethanol |
| 162 | 6-$CH_3$, 7-$CH_3$ | H | H, 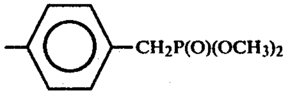 | 92 | 199–200 | Methanol |
| 163 | 6-$CH_3$, 7-$CH_3$ | H | H, 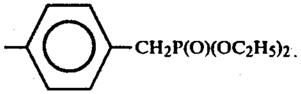 | 91 | 194–195 | Ethanol |
| 164 | 6-$CH_3$, 7-$CH_3$ | H | H, $-(CH_2)_2P(O)(OC_2H_5)_2$ | 46 | 100–101 | Ethyl acetate-hexane |
| 165 | 6-$CH_3$, 7-$CH_3$ | H | H, $-(CH_2)_3P(O)(OC_2H_5)_2$ | 48 | 107–108 | Ethyl acetate-hexane |
| 166 | 6-$CH_3$, 7-$CH_3$ | $CH_3$ | H, 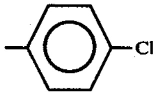 | 94 | Note 3) 207–208 | Ethyl acetate |
| 167 | 6-$CH_3$, 7-$CH_3$ | $CH_3$ | H, 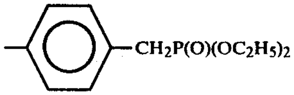 | 96 | Note 4) 94–95 | Ethyl acetate-hexane |

TABLE 18-continued
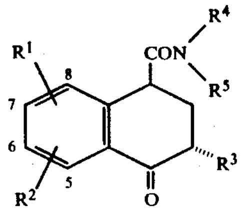
| Example No. | $R^1$, $R^2$ | $R^3$ | $R^4$, $R^5$ | Yield (%) | mp (°C.) | Recrystallization solvent |
|---|---|---|---|---|---|---|
| 168 | 6-$CH_3$, 7-$CH_3$ | $C_2H_5$ | H, 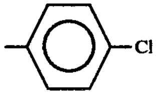 | 56 | Note 5) 236–237 | Ethyl acetate-hexane |
| 169 | 6-$CH_3$, 7-$CH_3$ | $C_2H_5$ | H, 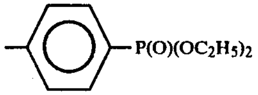 | 78 | Note 6) Oil | |
| 170 | 6-$CH_3$, 7-$CH_3$ | $C_2H_5$ | H, 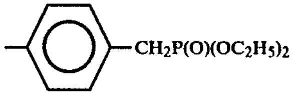 | 80 | Note 7) 67–68 | Ethyl acetate-hexane |
| 171 | 6-$CH_3$, 7-$CH_3$ | $C_3H_7$ | H, 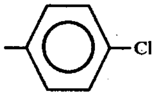 | 54 | 218–219 | Ethyl acetate |
| 172 | 6-$CH_3$, 7-$CH_3$ | $C_3H_7$ | H, 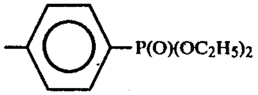 | 29 | Note 8) Oil | |
| 173 | 6-$CH_3$, 7-$CH_3$ | $C_3H_7$ | H, 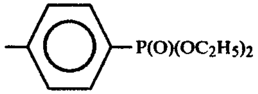 | 27 | Note 9) Oil | |
| 174 | 6-$CH_3$, 7-$CH_3$ | $C_3H_7$ | H, 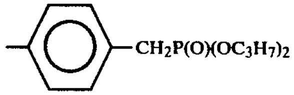 | 81 | Note 10) Oil | |

TABLE 18-continued
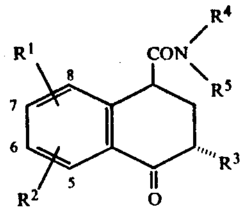
| Example No. | $R^1$, $R^2$ | $R^3$ | $R^4$, $R^5$ | Yield (%) | mp (°C.) | Recrystallization solvent |
|---|---|---|---|---|---|---|
| 175 | 6-$CH_3$, 7-$CH_3$ | 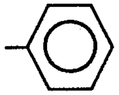 | H, 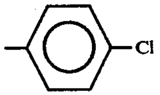 | 78 | 213–214 | Ethyl acetate-hexane |
| 176 | 6-$CH_3$, 7-$CH_3$ | 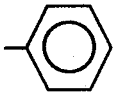 | H, 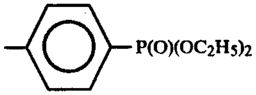 | 74 | 147–148 | Ethyl acetate-hexane |
| 177 | 6-$CH_3$, 7-$CH_3$ | 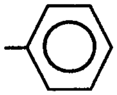 | H, 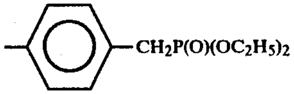 | 76 | 205–206 | Ethyl acetate |
| 178 | 6-$C_2H_5$, 7-$C_2H_5$ | H | H, 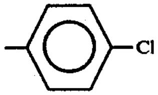 | 87 | 195–196 | Ethyl acetate-hexane |
| 179 | 6-$C_2H_5$, 7-$C_2H_5$ | H | H, 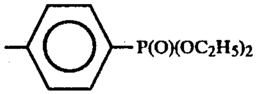 | 90 | 233–234 | Ethanol |
| 180 | 6-$C_2H_5$, 7-$C_2H_5$ | H | H, 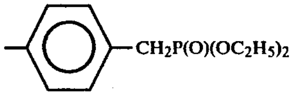 | 93 | 185–186 | Ethanol |

TABLE 18-continued
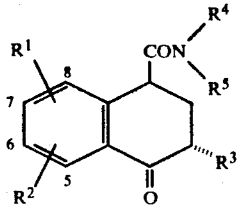
| Example No. | $R^1$, $R^2$ | $R^3$ | $R^4$, $R^5$ | Yield (%) | mp (°C.) | Recrystallization solvent |
|---|---|---|---|---|---|---|
| 181 | 6-$(CH_3)_2CH-$,<br>8-$(CH_3)_2CH-$ | H | H, 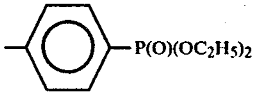 | 50 | 244-245 | Ethanol |
| 182 | 6-$(CH_3)_2CH-$,<br>8-$(CH_3)_2CH-$ | H | H, 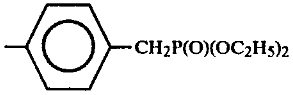 | 77 | 234-235 | Ethanol |
| 183 | 6,7-$(CH_2)_3-$ | H | H, 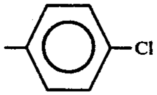 | 71 | 202-203 | Ethyl acetate |
| 184 | 6,7-$(CH_2)_3-$ | H | H, 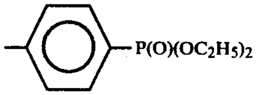 | 86 | 184-185 | Ethyl acetate |
| 185 | 6,7-$(CH_2)_3-$ | H | H, 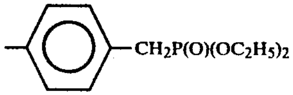 | 81 | 209-210 | Ethanol chloroform |
| 186 | 6,7-$(CH_2)_3-$ | H | H, $-(CH_2)_2P(O)(OC_2H_5)_2$ | 44 | 121-122 | Ethyl acetate-hexane |
| 187 | 6,7-$(CH_2)_3-$ | H | H, $-(CH_2)_3P(O)(OC_2H_5)_2$ | 38 | 119-120 | Ethyl acetate-hexane |
| 188 | 6,7-$(CH_2)_3-$ | $CH_3$ | H, 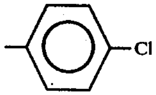 | 79 | 195-196 | Ethyl acetate-hexane |

TABLE 18-continued
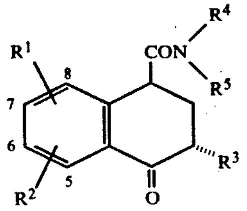
| Example No. | $R^1$, $R^2$ | $R^3$ | $R^4$, $R^5$ | Yield (%) | mp (°C.) | Recrystallization solvent |
|---|---|---|---|---|---|---|
| 189 | 6,7-$(CH_2)_3$— | $CH_3$ | H, 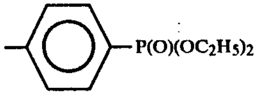 | 27 | 179–180 | Ethyl acetate |
| 190 | 6,7-$(CH_2)_3$— | $CH_3$ | H, 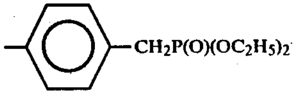 | 88 | 147–148 | Ethanol |
| 191 | 6,7-$(CH_2)_4$— | H | H, 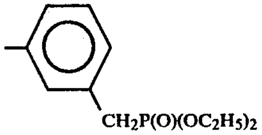 | 42 | 73–75 | Ethyl acetate-hexane |
| 192 | 6,7-$(CH_2)_4$— | H | H, 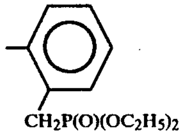 | 83 | 139–140 | Ethanol |
| 193 | 6,7-$(CH_2)_4$— | H | H, 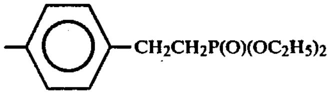 | 76 | 154–155 | Ethyl acetate-hexane |
| 194 | 6,7-$(CH_2)_4$— | $CH_3$ | H, 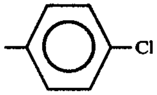 | 80 | Note 13) 212–213 | Ethyl acetate |

TABLE 18-continued
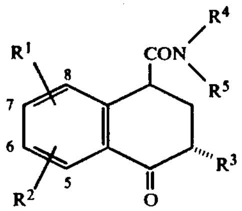
| Example No. | $R^1$, $R^2$ | $R^3$ | $R^4$, $R^5$ | Yield (%) | mp (°C.) | Recrystallization solvent |
|---|---|---|---|---|---|---|
| 195 | 6,7-$(CH_2)_4$— | $CH_3$ | H, 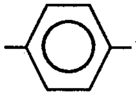 $P(O)(OC_2H_5)_2$ | 83 | Note 14) Oil | |
| 196 | 6,7-$(CH_2)_4$— | $CH_3$ | H, 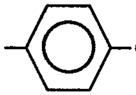 $CH_2P(O)(OC_2H_5)_2$ | 94 | Note 15) 108-109 | Ethyl acetate-hexane |
| 197 | 6,7-$(CH_2)_4$— | $CH_3$ | H, $-(CH_2)_3P(O)(OC_2H_5)_2$ | 45 | Note 16) Oil | |
| 198 | 6,7-$(CH_2)_5$— | H | H, 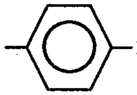 $P(O)(OC_2H_5)_2$ | 90 | 193-194 | Ethanol |
| 199 | 6,7-$(CH_2)_5$— | H | H, 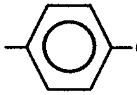 $CH_2P(O)(OC_2H_5)_2$ | 90 | 182-183 | Ethanol |

EXAMPLE 200

To a solution of 6,7-dimethyl-3,4-dihydro-1H-2-benzothiopyran-4-one-1-carboxylic acid (0.945 g) in THF (10 ml) were added oxalyl chloride (0.609 g) and DMF (2 drops), and the mixture was stirred at room temperature for 1 hour. On the other hand, a mixture of diethoxyphosphorylamine (4.9 g), sodium hydride in oil (60%, 0.32 g) and THF (30 ml) was stirred with ice-cooling for 30 minutes and, then, the above solution was added. The mixture was stirred with ice-cooling for 30 minutes, poured into water and extracted with ethyl acetate. The ethyl acetate layer was washed with water, dried ($MgSO_4$) and the solvent was distilled off to give N-diethoxyphosphoryl-6,7-dimethyl-3,4-dihydro-1H-2-benzothiopyran-4-one-1-carboxamide (0.29 g, 19%). Recrystallization from ethyl acetate gave colorless prisms melting at 192°-193½° C.

Elemental analysis, $C_{16}H_{22}NO_5PS$

Calcd.: C, 51.74; H, 5.97; N, 3.77.

Found: C, 51.71; H, 5.86; N, 3.74.

EXAMPLE 201

In substantially the same manner as Example 200, 6-cyclohexyl-N-diethoxyphosphoryl-3,4-dihyiro-1H-2-benzothiopyran-4-one-1-carboxamide was synthesized. Yield 36%. Recrystallization from ethyl acetate gave colorless needles melting at 163°-164° C.

Elemental analysis, $C_{20}H_{28}NO_5PS$

Calcd.: C, 56.46; H, 6.63; N, 3.29.

Found: C,56.37; H, 6.65; N, 3.09.

EXAMPLE 202

In THF (10 ml) was dissolved 6,7-dimethyl3,4-dihydro-1H-2-benzothiopyran-4-one-1-carboxylic acid (0.473 g) followed by addition of oxalyl chloride (0.305 g) and, then, DMF (1 drop). The mixture was stirred at room temperature for 2 hours. This reaction mixture was added to aqueous ammonia (20 ml)—ethyl acetate (40 ml) and the whole mixture was stirred at room temperature for 30 minutes. The ethyl acetate layer was then separated, washed with water, dried ($MgSO_4$) and the solvent was distilled off to give 6,7-dimethyl-3,4-dihydro-1H-2-benzothiopyran-4-one-1-carboxamide (0.38 g, 81%). Recrystallization from ethyl acetate gave colorless plates melting at 197°-198° C.

Elemental analysis, $C_{12}H_{13}NO_2S$

Calcd. C, 61.25; H, 5.57; N, 5.95.

Found: C, 61.20; H, 5.53; N, 6.00.

EXAMPLE 203

A mixture of 6,7-dimethyl-t-3-methyl-3,4-dihydro-1H-2-benzothiopyran-4-one-r-1-carboxylic acid (0.5 g) and thionyl chloride (2 ml) was refluxed with stirring for 1 hour, concentrated and the residue was dissolved in chloroform (3 ml). The solution was added to aqueous ammonia (20 ml)—ethyl acetate (30 ml), and the mixture was stirred at room temperature for 30 minutes. The ethyl acetate layer was separated, washed with water and dried ($MgSO_4$). The solvent was then distilled off to give 6,7-dimethyl-t-3-methyl-3,4-dihydro-1H-2-benzothiopyran-4-one-r-1-carboxamide (0.305 g, 61%). Recrystallization from ethyl acetate gave colorless needles melting at 190'-191° C.

Elemental analysis, $C_{12}H_{15}NO_2S$

Calcd.: C, 62.62; H, 6.06; N, 5.0.

Found: C, 62.69; H, 6.12; N, 5.63.

EXAMPLE 204

To a mixture of N-(4-diethoxyphosphorylphenyl)-6-cyclohexyl-3,4-dihydro-1H-2-benzopyran-4-one-1-carboxamide (1.8 g) and carbon tetrachloride (30 ml) was added iodotrimethylsilane (1.6 g) under ice-cooling, followed by stirring at room temperature for 30 minutes. The reaction mixture was concentrated, and methanol (30 ml) and 2N-HCl (100 ml) were added thereto in that order. The mixture was extracted with ethyl acetate, and the ethyl acetate layer was washed with water and dried ($MgSO_4$). The solvent was then distilled off to give 6-cyclohexyl-N-(4-phosphonophenyl)-3,4-dihydro-1H-2-benzothiopyran-4-one-1-carboxamide (0.92 g, 58%). Recrystallization from ethyl acetate—methanol gave colorless prisms melting at 232°-233° C.

Elemental analysis, $C_{22}H_{24}NO_5PS$

Calcd.: C, 59.32; H, b 5.43; N, 3.14.

Found: C, 58.90; H, 5.31; N, 3.02.

EXAMPLE 205

In substantially the same manner as Example 204, 6,7-dimethyl-N-(4-phosphonophenyl)-3,4-dihydro-1H-2-benzothiopyran-4-one-1-carboxamide was obtained. Yield 70%. Recrystallization from ethyl acetate—methanol gave colorless prisms melting at 262°-264° C.

Elemental analysis, $C_{18}H_{18}NO_5PS$

Calcd.: C, 55.25; H, 4.64; N, 3.58.

Found: C, 55.06; H, 4.72; N, 3.35.

EXAMPLE 206

To a solution of 6-cyclohexyl-N-(4-diethoxyphosphorylmethylphenyl)-3,4-dihydro-1H-2-benzothiopyran-4-one-1-carboxamide (2.6 g) in acetonitrile (50 ml) was added bromotrimethylsilane (3.1 g) and the mixture was stirred at room temperature for 12 hours. The reaction mixture was then poured into water and extracted with ethyl acetate. The ethyl acetate layer was washed with water, dried ($MgSO_4$) and the solvent was distilled off. The procedure yielded 6-cyclohexyl-N-(4-phosphonomethylphenyl)-3,4-dihyiro-1H-2-benzothiopyran-4-one-1-carboxamide (0.91 g, 40%). Recrystallization from ethyl acetate—methanol gave colorless prisms melting at 226°-227° C.

Elemental analysis, $C_{23}H_{26}NO_5PS$

Calcd.: C, 60.12; H, 5.70; N, 3.05.

Found: C, 59.71; H, 5.59; N, 2.98.

EXAMPLE 207

In substantially the same manner as Example 206, 6,7-dimethyl-N-(4-phosphonomethylphenyl)-3,4-dihydro-1H-2-benzothiopyran-4-one-1-carboxamide was synthesized. Recrystallization from ethyl acetate—methanol gave colorless prisms melting at 244°-245° C.

Elemental analysis, $C_{19}H_{20}NO_5PS$

Calcd.: C, 56.29; H, 4.97; N, 3.45.

Found: C, 55.97; H, 4.87; N, 3.34.

EXAMPLE 208

In substantially the same manner as Example 59, N-(4-chlorophenyl)-6,7-dimethyl-c-4-hydroxy-3,4-dihydro-1-H-2-benzothiopyran-r-1-carboxamide was obtained. Yield 78%. Recrystallization from ethanol-chloroform gave colorless prisms melting at 244°-245° C.

Elemental analysis, $C_{18}H_{18}NO_2SCl$

Calcd.: C, 62.15; H, 5.22; N, 4.03.

Found: C, 62.02; H, 5.18; N, 4.06.

EXAMPLE 209

In substantially the same manner as Example 59, N-(4-diethoxyphosphorylphenyl)-6,7-dimethyl-c-4-hydroxy-3-4-dihydro-1H-2-benzothiopyran-c-1-carboxamide was obtained. Recrystallization from ethyl acetate-hexane gave colorless prisms melting at 162°-163° C.

Elemental analysis, $C_{23}H_{30}NO_5PS$
Calcd.: C, 59.60; H, 6.52; N,3.20.
Found: C, 59.07: H, 6.55; N, 2.99.

PREPARATION EXAMPLE 1

Tablets

Composition per tablet
(1) Compound (the compound synthesized in Example 22) 50 mg
(2) Corn starch 30 mg
(3) Lactose 113.4 mg
(4) Hydroxypropylcellulose 6 mg
(5) Water 0.03 ml
(6) Magnesium stearate 0.6 mg Of the above ingredients, (1), (2), (3) and (4) were blended and kneaded with (5) and the resulting mass was d.ried in vacuo at 40° C. for 16 hours.

The mass was pulverized and sieved through a 16-mesh screen to give granules. The granules were mixed with (6) and the composition was compression-molded with a rotary tablet-making machine (manufactured by Kikusui Seisakusho Co., Ltd.) to give 200 mg tablets.

PREPARATION EXAMPLE 2

Enteric-coated tablets (1) Compound (the compound synthesized in Example 146) 50 mg
(2) Corn starch 30 mg
(3) Lactose 113.4 mg
(4) Hydroxycellulose 6 mg
(5) Water 0.03 ml
(6) Magnesium stearate 0.6 mg
(7) Cellulose acetate phthalate 10 mg
(8) Acetone 0.2 ml Of the above ingredients, (1), (2), (3), (4), (5) and (6) were used to give tablets in the same manner as Preparation Example 1. The tablets were film-coated with an acetone solution of (7) using a bar coater (manufactured by Freund) to give 210 mg enteric tablets.

PREPARATION EXAMPLE 3

Capsules (1) Compound (the compound synthesized in Example 163) 30 mg
(2) Corn starch 40 mg
(3) Lactose 74 mg
(4) Hydroxypropylcellulose 6 mg
(5) Water 0.02 ml Of the above ingredients, (1), (2), (3) and (4) were blended and kneaded with (5) and the reuslting mass was dried in vacuo at 40° C. for 16 hours. The dried mass was pulverized and sieved through a 16-mesh screen to give granules. Using a capsule filling machine (Zanassi, Italy), the granules were filled into No. 3 gelatin capsules to give capsules.

PREPARATION EXAMPLE 4

Injection (1) Compound (the compound synthesized in Example 23) 5 mg
(2) Sodium salicylate 50 mg
(3) Sodium chloride 180 mg
(4) Sodium metabisulfite 20 mg
(5) Methylparaben 36 mg pylparaben 4 mg
(6) Propylparaben 4 mg
(7) Distilled water for injection 2 ml Of the above ingredients, (2), (3), (4), (5) and (6) were dissolved in one-half of the indicated volume of distilled water for injection with stirring at 80° C. After the resulting solution was cooled to 40° C., (1) was dissolved in the solution. To the solution thus obtained was added the remaining volume of distilled water for injection to make the indicated volume and aseptically filtered through an appropriate filter paper to give a sterile injectable solution.

We claim:

1. A sulfur-containing heterocyclic compound of the formula (I)

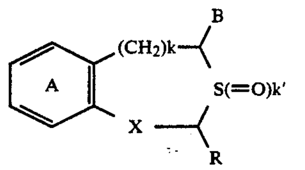

wherein ring A is a benzene ring which may be substituted by 1 to 4 substituents, which are the same or different, selected from the group conssitng of:

(1) halogen,
(2) nitro,
(3) $C_{1-10}$ straight-chain or branched alkyl or $C_{3-7}$ cycloalkyl group which may be substituted by 1 to 3 substituents, which are the same or different, selected from a group consisting of a halogen, hydroxyl, $C_{1-6}$ alkoxy, mono- or di($C_{1-6}$ alkoxy)phosphoryl and phosphono group,
(4) (i) hydroxyl, or
(ii) $C_{110}$ straight-chain or branched alkoxy, $C_{4-6}$ cycloalkoxy, $C_{2-10}$ alkenyloxy, $C_{6-19}$ aralkyloxy, $C_{2-10}$ alkanoxyloxy or $C_{6-14}$ aryloxy group which may be substituted by 1 to 3 substituents, which are the same or different, selected from a group consisting of the halogen, hydroxyl, $C_{1-6}$ alkoxy and mono- or di($C_{1-6}$ alkoxy) phosphoryl group,
(5)(i) thiol, or
(ii) $C_{1-10}$ straight-chain or branched alkylthio, $C_{4-6}$ cycloalkylthio, $C_{7-19}$ aralkylthio or $C_{2-10}$ alkanoylthio group which may be substituted by 1 to 3 substituents, which are the same or different, selected from a group consisting of a halogen, hydroxyl, $C_{1-6}$ alkoxy and mono- or di($C_{1-6}$ alkoxy)phosphoryl gorup,
(6)amino group which may be substituted by 1 or 2 substituents, which are the same or different, selected from a group consisting of a $C_{1-10}$ alkyl, $C_{2-10}$ alkenyl, $C_{6-14}$ aryl and $C_{7-19}$ aralkyl group wherein the substitutent may be further substituted by a halogen, $C_{1-3}$ alkoxy, mono- or di($C_{1-6}$ alkoxy)phosphoryl or phosphono group,
(7) $C_{1-19}$ acyl group,
(8) mono- or dialkoxyphosphoryl, (9) phosphono

(10) aryl group which may be substituted by 1 to 3 substituents, which are the same or different, selected from a group consisting of a $C_{1-6}$ alkyl, halogen, hydroxyl and $C_{1-6}$ alkoxy group,

(11) $C_{7-19}$ aralkyl group which may be substituted by 1 to 3 substituents, which are the same or different, selected from a group consisting of a $C_{1-6}$ alkyl, halogen, hydroxyl and $c_{1-6}$ alkoxy group and

(12) 5- or 6-membered aromatic heterocyclic group having 1 to 4 nitrogen, oxygen and/or sulfur atoms, which may be substituted by 1 to 3 substituents, which are the same or different, selected from a group consisting of a $C_{1-6}$ alkyl, halogen, hydroxyl and $C_{1-6}$ alkoxy group;

R is (i) a hydrogen atom or (ii) a $C_{1-10}$ alkyl, $C_{2-10}$ alkenyl, $C_{6-14}$ aryl or $C_{7-19}$ aralkyl group which may be substituted by a 5- or 6-membered aromatic heterocyclic group having 1 to 4 nitrogen, oxygen and/or sulfur atoms, halogen, dialkoxyphosphoryl or phosphono group;

B is a carboxyl, $C_{1-10}$ alkoxy carbonyl, $C_{6-14}$ aryloxycarbonyl, $C_{7-19}$ aralkyloxycarbonyl group or a group of the formula —$CONR_1R_2$ where $R_1$ and $R_2$ each is (1) a hydrogen atom, (2) a $C_{1-10}$ alkyl, $C_{2-10}$ alkenyl, $C_{6-14}$ aryl or $C_{7-19}$ aralkyl group which may be substituted by 1 to 3 substituents, which are the same or different, selected from a group consisting of (i) a halogen, (ii) hydroxyl, (iii) $C_{1-6}$ alkoxy, (iv) amino which may be substituted by $C_{1-6}$ alkyl, (v) amino substituted by acyl, (vi) carbamoyl which may be substituted by $C_{1-6}$ alkyl, (vii) $C_{1-6}$ alkoxycarbonyl, (viii) mono- or dialkoxyphosphoryl (ix) phosphono group and (x) 5- or 6-membered aromatic heterocyclic group having 1 to 4 nitrogen, oxygen and/or sulfur atoms, (3)

(i) 5- to 7-membered unsubstituted heterocycles containing one sulfur, nitrogen or oxygen atom, 5- or 6-membered heterocycles containing 2 to 4 nitrogen atoms, or 5- or 6-membered heterocycles containing 1 to 2 nitrogen atoms and one sulfur or oxygen atom, and each of these heterocycles being optionally fused to a 6-membered ring contaiing a maximum of 2 nitrogen atoms, a benzene ring, or a 5-membered ring containing one sulfur atom or (ii) substituted heterocycles selected from the group consisting of 5-chloro-2-pyridyl, 3-methoxy-2-pyridyl, 5-methyl-2-benzothiazoly, 5-methyl-4-phenyl-2-thiazolyl, 3-phenyl-5-isooxazolyl, 4-(4-chlorophenyl)-5-methyl-2-oxazolyl, 3-phenyl-1,2,4-thiadiazol-5yl, 5-methyl-1,3,4-thiadiazol-2-yl, 5-acetylamino-2-pyrimidyl, 3-methyl-2-thienyl, 4,5-dimethyl-2-furanyl or 4-methyl-2-morpholinyl or alternatively $R_1$ and $R_2$, taken together with the adjacent nitrogen atom, form morpholine, piperidine, thiomorpholine, homopiperidine, pyrrolidine or thiazolidine, x is —CH(OH)— or —CO—; k is 0 or 1, and k' is 0, 1 or 2 or a pharmaceutically acceptable salt thereof.

2. A compound as claimed in cliam 1, wherein B is a $C_{1-10}$ alkoxycarbonyl group or a group of the formula —$CONR_1R_2$ where $R_1$ and $R_2$ each is (1) a hydrogen atom, (2) a $C_{1-10}$ alkyl, $C_{2-10}$ alkenyl, $C_{6-14}$ aryl or $C_{7-19}$ aralkyl group which may be substituted by 1 to 3 substituents, which are the same or different, selected from a group consisting of (i) a halogen, (ii) hydroxyl, (iii) $C_{1-6}$ alkoxy, (iv) amino which may be substituted by $C_{1-6}$ alkyl, (v) amino substituted by acyl, (vi) carbamoyl which may be substituted by $C_{1-6}$ alkyl, (vi) carbamoyl which may be substituted by $C_{1-6}$ alkyl, (vii) $C_{1-6}$ alkoxycarbonyl, (viii) mono- or dialkoxyphosphoryl (ix) phosphono group and (x) 5- or 6-membered aromatic heterocyclic group having 1 to 4 nitrogen, oxygen and/or sulfur atoms, (3)

(i) 5- to 7-membered unsubstituted heterocycles containing one sulfur, nitrogen or oxygen atom, 5- or 6-membered heterocycles containing 2 to 4 nitrogen atoms, or 5- or 6-membered heterocycles containing 1 to 2 nitrogen atoms and one sulfur or oxygen atom, and each of these heterocycles being optionally fused to a 6-membered ring contaiing a maximum of 2 nitrogen atoms, a benzene ring, or a 5-membered ring containing one sulfur atom or (ii) substituted heterocycles selected from the group consisting of 5-chloro-2-pyridyl, 3-methoxy-2-pyridyl, 5-methyl-2-benzothiazoly, 5-methyl-4-phenyl-2-thiazolyl, 3-phenyl-5-isooxazolyl, 4-(4-chlorophenyl)-5-methyl-2-oxazolyl, 3-phenyl-1,2,4-thiadiazol-5yl, 5-methyl-1,3,4-thiadiazol-2-yl, 5-acetylamino-2-pyrimidyl, 3-methyl-2-thienyl, 4,5-dimethyl-2-furanyl or 4-methyl-2-morpholinyl or alternatively $R_1$ and $R_2$, taken together with the adjacent nitrogen atom, form morpholine, piperidine, thiomorpholine, homopiperidine, pyrrolidine or thiazolidine.

3. A compound as claimed in claim 1, wherein B is a group of the formula —$CONR_1R_2$ where $R_1$ and $R_1$ each is (1) a hydrogen atom, (2) a $C_{1-10}$ alkyl, $C_{2-10}$ alkenyl, $C_{6-14}$ aryl or $C_{7-19}$ aralkyl group which may be substituted by 1 to 3 substituents, which are the same or different, selected from a group consisting of (i) a halogen, (ii) hydroxyl, (iii) $C_{1-6}$ alkoxy, (iv) amino which may be substituted by $C_{1-6}$ alkyl, (v) amino substituted by acyl, (vi) carbamoyl which may be substituted by $C_{1-6}$ alkyl, (vii) $C_{1-6}$ alkoxycarbonyl, (viii) mono- or dialkoxyphosphoryl (ix) phosphono group and (x) 5- or 6-membered aromatic heterocyclic group having 1 to 4 nitrogen, oxygen and/or sulfur atoms, (3)

(i) 5- to 7-membered unsubstituted heterocycles containing one sulfur, nitrogen or oxygen atom, 5- or 6-membered heterocycles containing 2 to 4 nitrogen atoms, or 5- or 6-membered heterocycles containing 1 to 2 nitrogen atoms and one sulfur or oxygen atom, and each of these heterocycles being optionally fused to a 6-membered ring contaiing a maximum of 2 nitrogen atoms, a benzene ring, or a 5-membered ring containing one sulfur atom or (ii) substituted heterocycles selected from the group consisting of 5-chloro-2-pyridyl, 3-methoxy-2-pyridyl, 5-methyl-2-benzothiazoly, 5-methyl-4-phenyl-2-thiazolyl, 3-phenyl-5-isooxazolyl, 4-(4-chlorophenyl)-5-methyl-2-oxazolyl, 3-phenyl-1,2,4-thiadiazol-5yl, 5-methyl-1,3,4-thiadiazol-2-yl, 5-acetylamino-2-pyrimidyl, 3-methyl-2-thienyl, 4,5-dimethyl-2-furanyl or 4-methyl-2-morpholinyl or alternatively $R_1$ and $R_2$, taken together with the adjacent nitrogen atom, form morpholine, piperidine, thiomorpholine, homopiperidine, pyrrolidine or thiazolidine.

4. A compound as claimed in claim 1, wherein ring A is a benzene ring which may be substituted by 1 or 2 substituents, which are the same or different, selected from a group consisting of a halogen, a$c_{1-10}$ alkyl and a $C_{1-6}$ akoxy; R is a hydrogen atom, a $C_{1-10}$ alkyl or a phenyl group; B is a $C_{1-10}$ alkoxycarbonyl group of a group of the formula —$CONR_1R_2$ where $R_1$ and $R_2$ each is (1) a hydrogen atom, (2) a $C_{1-10}$ alkyl, $C_{2-10}$ alkenyl, $C_{6-14}$ aryl or $C_{7-19}$ aralkyl group which may be substituted by 1 to 3 substituents, which are the same or different, selected from a group consisting of (i) a halogen, (ii) hydroxyl, (iii) $C_{1-6}$ alkoxy, (iv) amino which may be substituted by $C_{1-6}$ alkyl, (v) amino substituted by acyl, (vi) carbamoyl which may be substituted by $C_{1-6}$ alkyl, (vii) $C_{1-6}$ alkoxycarbonyl, (viii) mono- or dialkoxyphosphoryl (ix) phosphono group and (x) 5- or 6-membered aromatic heterocyclic group having 1 to 4 nitrogen, oxygen and/or sulfur atoms, (3)

(i) 5- to 7-membered unsubstituted heterocycles containing one sulfur, nitrogen or oxygen atom, 5- or 6-membered heterocycles containing 2 to 4 nitrogen atoms, or 5- or 6-membered heterocycles containing 1 to 2 nitrogen atoms and one sulfur or oxygen atom, and each of these heterocycles being optionally fused to a 6-membered ring contaiing a maximum of 2 nitrogen atoms, a benzene ring, or a 5-membered ring containing one sulfur atom or (ii) substituted heterocycles selected from the group consisting of 5-chloro-2-pyridyl, 3-methoxy-2-pyridyl, 5-methyl-2-benzothiazoly, 5-methyl-4-phenyl-2-thiazolyl, 3-phenyl-5-isooxazolyl, 4-(4-chlorophenyl)-5-methyl-2-oxazolyl, 3-phenyl-1,2,4-thiadiazol-5yl, 5-methyl-1,3,4-thiadiazol-2-yl, 5-acetylamino-2-pyrimidyl, 3-methyl-2-thienyl, 4,5-dimethyl-2-furanyl or 4-methyl-2-morpholinyl or alternatively $R_1$ and $R_2$, taken together with the adjacent nitrogen atom, form morpholine, piperidine, thiomorpholine, homopiperidine, pyrrolidine or thiazolidine, and each of K and k' is 0.

5. A compound as claimed in claim 1 wherein ring A is a benzene ring which may be substituted by 1 or 2 substituents, which are the same or different, selected from a group consisting of a halogen, a $C_{1-10}$ alkyl and a $C_{1-6}$ alkoxy.

6. A compound as claimed in claim 1 wherein ring A is a benzene ring which may be substituted by 1 or 2 $C_{1-10}$ alkyl groups, which are the same or different.

7. A compound as claimed in claim 1 wherein ring A is a benzene ring which may be substituted by a $C_{3-7}$ cycloalkyl group.

8. A compound as claimed in claim 1 wherein R is a hydrogen atom, a $C_{1-10}$ alkyl or a phenyl group.

9. A compound as claimed in claim 1 wherein R is a hydrogen atom or a methyl group.

10. A compound as claimed in laim 2 wherein $R_1$ is a hydrogen atom and $R_2$ is a group of the formula $C_6C_4(CH_2)_nP(O)(OR')_2$ where n is 0 or 1 and R' is a $C_{1-6}$ alkyl group.

11. A compound as claimed in claim 1, namely 6-cyclohexyl-N-(4-diethoxyphosphorylmethylphenyl)-3,4-dihydro-1H-2-benzothiopyran-4-one-1-carboxamide.

12. A compound as claimed in claim 1, namely 6,7-dimethyl-N-(4-diethoxyphosphorylphenyl)-3,4-dihydro-1H-2-benzothiopyran-4-one-1-carboxamide.

13. A compound as claimed in claim 1, namely 6,7-dimethyl-N-(4-diethoxyphophorylmethylphenyl)-3,4-dihydro-1H-2-benzothipyran-4-one-1-carboxamide.

14. A pharmaceutical preparation for use in the treatment of osteoporosis comprising an effective antiosteoporotic amount of a compound or pharmaceutically acceptable salt claimed in claim 1 and a pharmaceutically acceptable carrier or diluent.

* * * * *